United States Patent [19]
Sadowski et al.

[11] Patent Number: 5,697,917
[45] Date of Patent: Dec. 16, 1997

[54] NOZZLE ASSEMBLY WITH ADJUSTABLE PLUNGER TRAVEL GAP

[75] Inventors: Peter L. Sadowski, Woodbury, Minn.; David Schiff, Highland Park, N.J.; Paul Mulhauser, New York, N.Y.

[73] Assignee: Medi-Ject Corporation, Minneapolis, Minn.

[21] Appl. No.: 609,146

[22] Filed: Feb. 29, 1996

[51] Int. Cl.⁶ ............................................. A61M 5/00
[52] U.S. Cl. ........................ 604/218; 604/68; 604/70
[58] Field of Search ........................ 604/218, 68–72, 604/228, 229, 239, 232

[56] References Cited

U.S. PATENT DOCUMENTS

| | | |
|---|---|---|
| D. 304,616 | 11/1989 | Dunlap et al. . |
| D. 349,958 | 8/1994 | Hollis et al. . |
| 396,107 | 1/1889 | Nickerson . |
| 489,757 | 1/1893 | Reilly . |
| 1,567,517 | 12/1925 | Kisbey . |
| 1,973,706 | 9/1934 | Hawley . |
| 2,322,244 | 6/1943 | Lockhart . |
| 2,322,245 | 6/1943 | Lockhart . |
| 2,380,534 | 7/1945 | Lockhart . |
| 2,390,246 | 12/1945 | Folkman . |
| 2,398,544 | 4/1946 | Lockhart . |
| 2,413,303 | 12/1946 | Folkman . |
| 2,459,875 | 1/1949 | Folkman . |
| 2,547,099 | 4/1951 | Smoot . |
| 2,605,763 | 8/1952 | Smoot . |
| 2,635,602 | 4/1953 | Hein . |
| 2,653,602 | 9/1953 | Smoot . |
| 2,670,121 | 2/1954 | Scherer et al. . |
| 2,671,347 | 3/1954 | Scherer . |
| 2,681,653 | 6/1954 | Kuhne . |
| 2,688,968 | 9/1954 | Scherer . |
| 2,699,166 | 1/1955 | Dickinson, Jr. et al. . |
| 2,704,542 | 3/1955 | Scherer . |
| 2,704,543 | 3/1955 | Scherer . |
| 2,705,953 | 4/1955 | Potez . |
| 2,714,887 | 8/1955 | Venditty . |
| 2,717,597 | 9/1955 | Hein, Jr. . |
| 2,737,946 | 3/1956 | Hein, Jr. . |
| 2,754,818 | 7/1956 | Scherer . |
| 2,762,369 | 9/1956 | Venditty . |
| 2,762,370 | 9/1956 | Venditty . |

(List continued on next page.)

FOREIGN PATENT DOCUMENTS

| | | |
|---|---|---|
| 2028870 | 5/1991 | Canada . |
| 2071115 | 12/1992 | Canada . |
| 0 157 906 | 10/1985 | European Pat. Off. . |
| 0 460 961 | 6/1991 | European Pat. Off. . |
| 2254 153 A | 5/1974 | Germany . |
| 76202162 | 5/1986 | Taiwan . |
| 959397 | 6/1964 | United Kingdom . |
| WO 93/03779 | 3/1993 | WIPO . |
| WO 95/03844 | 2/1995 | WIPO . |
| WO 96/21482 | 7/1996 | WIPO . |

OTHER PUBLICATIONS

Catalog: Hoechst Celanese—Advanced Materials Group, "Vectra©Liquid Crystal Polymer".
Catalog: Industrial Gas Springs, Ltd. Date Unavailable.

*Primary Examiner*—John D. Yasko
*Attorney, Agent, or Firm*—Pennie & Edmonds LLP

[57] ABSTRACT

The present invention relates to a nozzle assembly adapted for use with an injector device having an energy generating source and a chamber adapted for holding a fluid and having first and second end portions with an orifice defined at the first end portion for passage of the fluid and being open at the second end portion. The device includes a first driving member movably positioned in the chamber; a second driving member movably positioned in the chamber and spaced apart from the first driving member according to a predetermined travel distance and including an end portion operative for expelling fluid out of or drawing fluid into the chamber via the orifice; and a spacing member disposed between the first and second driving members for maintaining said predetermined travel distance during displacement of the first and second driving members before the energy generating source is activated.

21 Claims, 16 Drawing Sheets

U.S. PATENT DOCUMENTS

| | | |
|---|---|---|
| 2,764,977 | 10/1956 | Ferguson . |
| 2,789,839 | 4/1957 | Siebert . |
| 2,798,485 | 7/1957 | Hein, Jr. . |
| 2,798,486 | 7/1957 | Hein, Jr. . |
| 2,800,903 | 7/1957 | Smoot . |
| 2,816,543 | 12/1957 | Venditty et al. . |
| 2,816,544 | 12/1957 | Scherer et al. . |
| 2,820,655 | 1/1958 | Hileman . |
| 2,821,193 | 1/1958 | Ziherl et al. . |
| 2,821,981 | 2/1958 | Ziherl et al. . |
| 2,825,332 | 3/1958 | Johnson . |
| 2,902,994 | 9/1959 | Scherer . |
| 2,921,582 | 1/1960 | Sadd . |
| 2,928,390 | 3/1960 | Venditty et al. . |
| 3,057,349 | 10/1962 | Ismach . |
| 3,066,570 | 12/1962 | Stauffer . |
| 3,115,133 | 12/1963 | Morando . |
| 3,123,070 | 3/1964 | Kath . |
| 3,129,708 | 4/1964 | Krantz . |
| 3,130,723 | 4/1964 | Venditty et al. . |
| 3,131,692 | 5/1964 | Love . |
| 3,138,157 | 6/1964 | Ziherl et al. . |
| 3,140,713 | 7/1964 | Ismach . |
| 3,147,967 | 9/1964 | Bougeard . |
| 3,167,071 | 1/1965 | Venditty . |
| 3,189,029 | 6/1965 | Stephens . |
| 3,202,151 | 8/1965 | Kath . |
| 3,245,703 | 4/1966 | Manly . |
| 3,292,622 | 12/1966 | Banker . |
| 3,308,818 | 3/1967 | Rutkowski . |
| 3,330,276 | 7/1967 | Gordon . |
| 3,330,277 | 7/1967 | Gabriels . |
| 3,335,722 | 8/1967 | Lowry et al. . |
| 3,353,537 | 11/1967 | Knox et al. . |
| 3,406,684 | 10/1968 | Tsujino . |
| 3,424,154 | 1/1969 | Kinsley . |
| 3,461,867 | 8/1969 | Zimmet et al. . |
| 3,476,110 | 11/1969 | Yahner . |
| 3,490,451 | 1/1970 | Yahner . |
| 3,507,276 | 4/1970 | Burgess . |
| 3,518,990 | 7/1970 | Banker . |
| 3,521,633 | 7/1970 | Yahner . |
| 3,526,225 | 9/1970 | Isobe . |
| 3,527,212 | 9/1970 | Clark . |
| 3,557,784 | 1/1971 | Shields . |
| 3,561,443 | 2/1971 | Banker . |
| 3,625,208 | 12/1971 | Frost et al. . |
| 3,659,587 | 5/1972 | Baldwin . |
| 3,688,765 | 9/1972 | Gasaway . |
| 3,714,943 | 2/1973 | Yanof et al. . |
| 3,768,472 | 10/1973 | Hodosh et al. . |
| 3,779,371 | 12/1973 | Rovinski . |
| 3,782,380 | 1/1974 | Van Der Gaast . |
| 3,783,895 | 1/1974 | Weichselbaum . |
| 3,788,315 | 1/1974 | Laurens . |
| 3,805,783 | 4/1974 | Ismach . |
| 3,827,601 | 8/1974 | Magrath et al. . |
| 3,838,689 | 10/1974 | Cohen . |
| 3,908,651 | 9/1975 | Fudge . |
| 3,938,520 | 2/1976 | Scislowicz et al. . |
| 3,945,379 | 3/1976 | Pritz et al. . |
| 3,945,383 | 3/1976 | Bennett et al. . |
| 4,059,107 | 11/1977 | Iriguchi et al. . |
| 4,089,334 | 5/1978 | Schwebel et al. . |
| 4,328,802 | 5/1982 | Curley et al. . |
| 4,387,879 | 6/1983 | Tauschinski . |
| 4,421,508 | 12/1983 | Cohen . |
| 4,447,225 | 5/1984 | Taff et al. . |
| 4,500,075 | 2/1985 | Tsuchiya et al. . |
| 4,505,709 | 3/1985 | Froning et al. . |
| 4,507,113 | 3/1985 | Dunlap . |
| 4,518,385 | 5/1985 | Lindmayer et al. . |
| 4,561,856 | 12/1985 | Cochran . |
| 4,588,403 | 5/1986 | Weiss et al. . |
| 4,596,556 | 6/1986 | Morrow et al. . |
| 4,619,651 | 10/1986 | Kopfer et al. . |
| 4,623,332 | 11/1986 | Lindmayer et al. . |
| 4,626,242 | 12/1986 | Fejes et al. . |
| 4,662,878 | 5/1987 | Lindmayer . |
| 4,675,020 | 6/1987 | McPhee . |
| 4,680,027 | 7/1987 | Parsons et al. . |
| 4,709,686 | 12/1987 | Taylor et al. . |
| 4,722,728 | 2/1988 | Dixon . |
| 4,744,786 | 5/1988 | Hooven . |
| 4,768,568 | 9/1988 | Fournier et al. . |
| 4,771,758 | 9/1988 | Taylor et al. . |
| 4,775,173 | 10/1988 | Sauer . |
| 4,790,824 | 12/1988 | Morrow et al. . |
| 4,834,149 | 5/1989 | Fourier et al. . |
| 4,850,967 | 7/1989 | Cosmai . |
| 4,863,427 | 9/1989 | Cocchi . |
| 4,874,367 | 10/1989 | Edwards . |
| 4,883,483 | 11/1989 | Lindmayer . |
| 4,909,488 | 3/1990 | Seibert et al. . |
| 4,923,072 | 5/1990 | Rilliet . |
| 4,940,460 | 7/1990 | Casey et al. . |
| 4,941,880 | 7/1990 | Burns . |
| 4,948,104 | 8/1990 | Wirges . |
| 4,950,240 | 8/1990 | Greenwood ................. 604/110 |
| 4,989,905 | 2/1991 | Rajecki . |
| 5,024,656 | 6/1991 | Gasaway et al. ............. 607/70 |
| 5,031,266 | 7/1991 | Tillman et al. . |
| 5,041,715 | 8/1991 | Muller . |
| 5,061,263 | 10/1991 | Yamazaki et al. . |
| 5,062,830 | 11/1991 | Dunlap . |
| 5,064,413 | 11/1991 | McKinnon et al. . |
| 5,066,280 | 11/1991 | Braithwaite . |
| 5,073,165 | 12/1991 | Edwards . |
| 5,085,332 | 2/1992 | Gettig et al. . |
| 5,116,313 | 5/1992 | McGregor . |
| 5,135,507 | 8/1992 | Haber et al. . |
| 5,161,786 | 11/1992 | Cohen . |
| 5,165,560 | 11/1992 | Ennis, III et al. . |
| 5,176,406 | 1/1993 | Straghan . |
| 5,181,912 | 1/1993 | Hammett ................... 604/110 |
| 5,188,599 | 2/1993 | Botich et al. ............. 604/110 |
| 5,190,523 | 3/1993 | Lindmayer . |
| 5,193,517 | 3/1993 | Taylor et al. . |
| 5,209,362 | 5/1993 | Lutzker . |
| 5,224,932 | 7/1993 | Lappas . |
| 5,226,882 | 7/1993 | Bates . |
| 5,281,202 | 1/1994 | Weber et al. . |
| 5,292,308 | 3/1994 | Ryan . |
| 5,304,128 | 4/1994 | Haber et al. . |
| 5,312,335 | 5/1994 | McKinnon et al. . |
| 5,312,577 | 5/1994 | Peterson et al. . |
| 5,316,198 | 5/1994 | Fuchs et al. . |
| 5,334,144 | 8/1994 | Alchas et al. . |
| 5,352,203 | 10/1994 | Vallelunga et al. .......... 604/110 |
| 5,356,380 | 10/1994 | Hoekwater et al. . |
| 5,360,146 | 11/1994 | Ikushima . |
| 5,383,851 | 1/1995 | McKinnon, Jr. et al. . |
| 5,399,163 | 3/1995 | Peterson et al. . |
| 5,407,431 | 4/1995 | Botich et al. . |
| 5,413,471 | 5/1995 | Yamauchi ................ 425/129.1 |
| 5,423,756 | 6/1995 | Van der Merwe . |
| 5,480,381 | 1/1996 | Weston ..................... 604/68 |
| 5,499,972 | 3/1996 | Parsons .................... 604/68 |
| 5,503,627 | 4/1996 | McKinnon et al. .......... 604/72 |
| 5,520,639 | 5/1996 | Peterson et al. ............ 604/68 |
| 5,569,189 | 10/1996 | Weston .................... 604/68 |

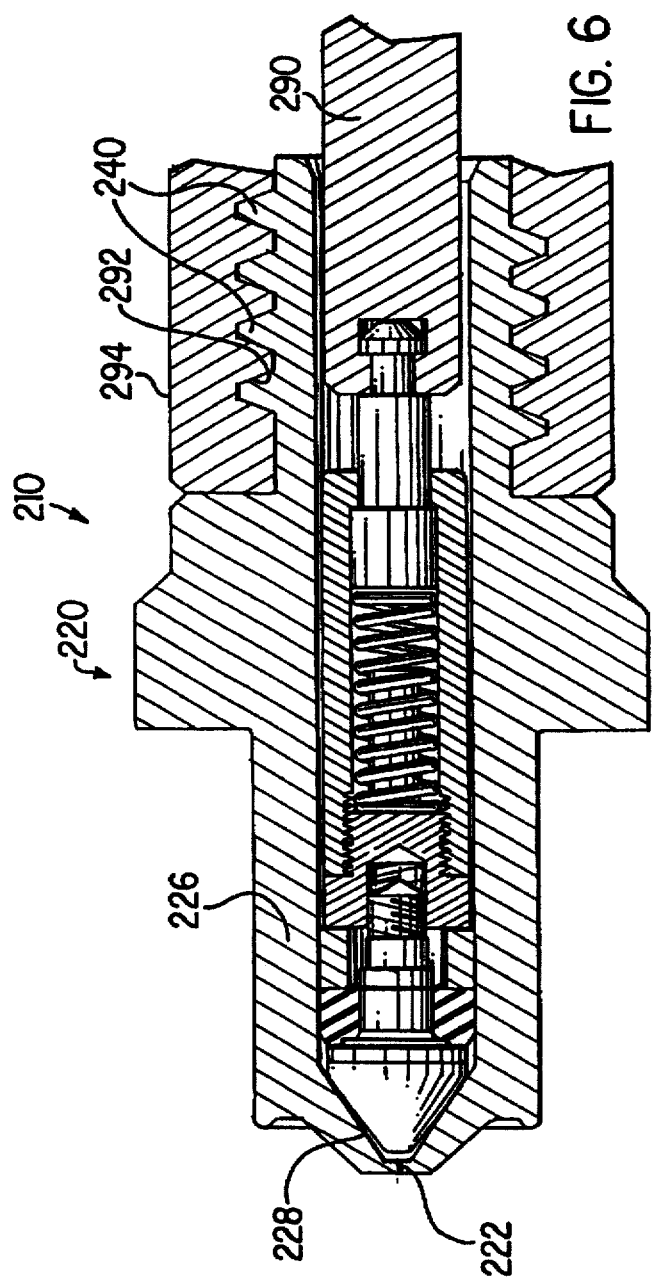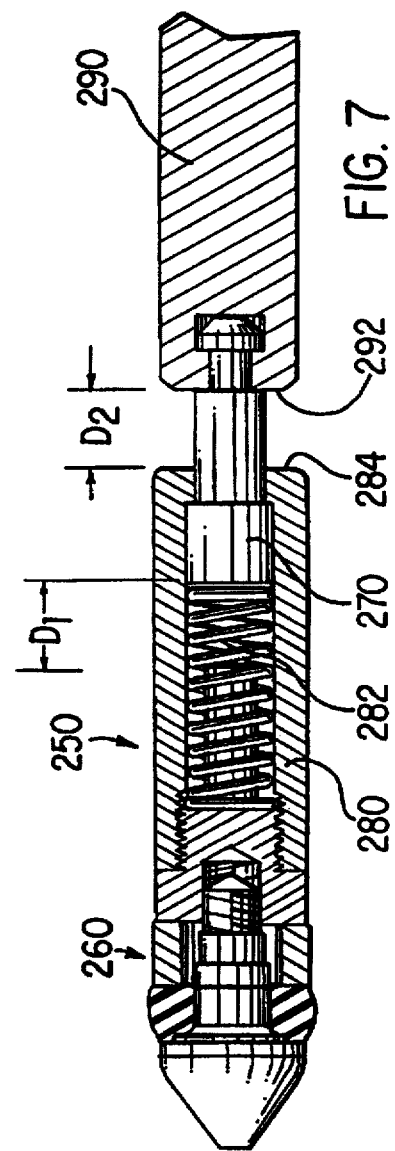

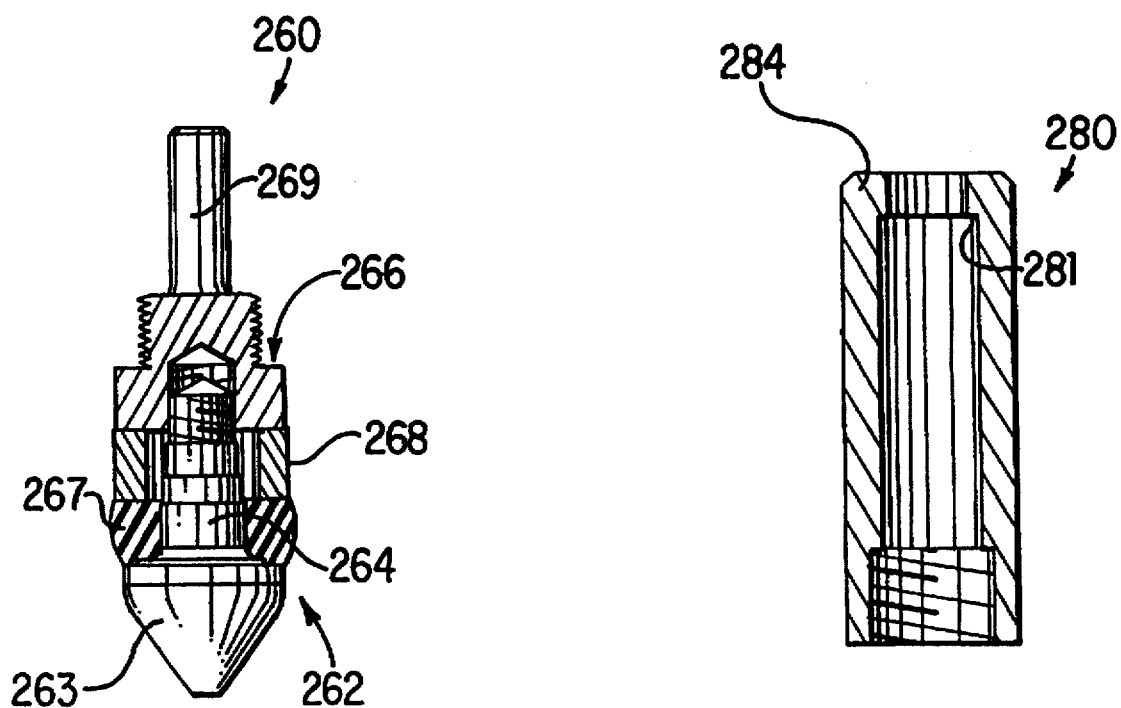
FIG. 8
FIG. 9
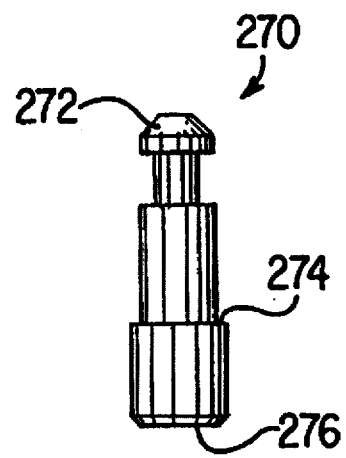
FIG. 10

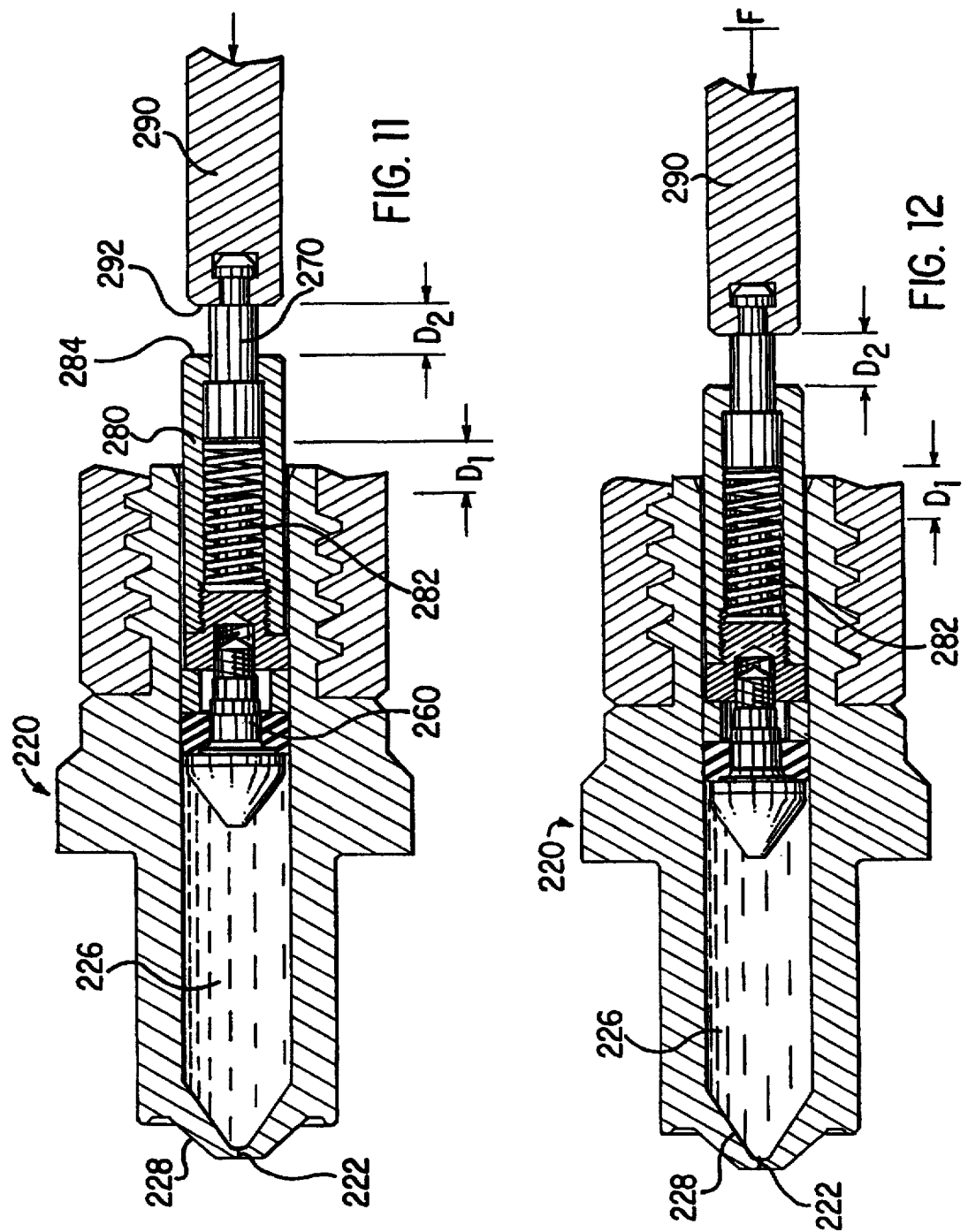

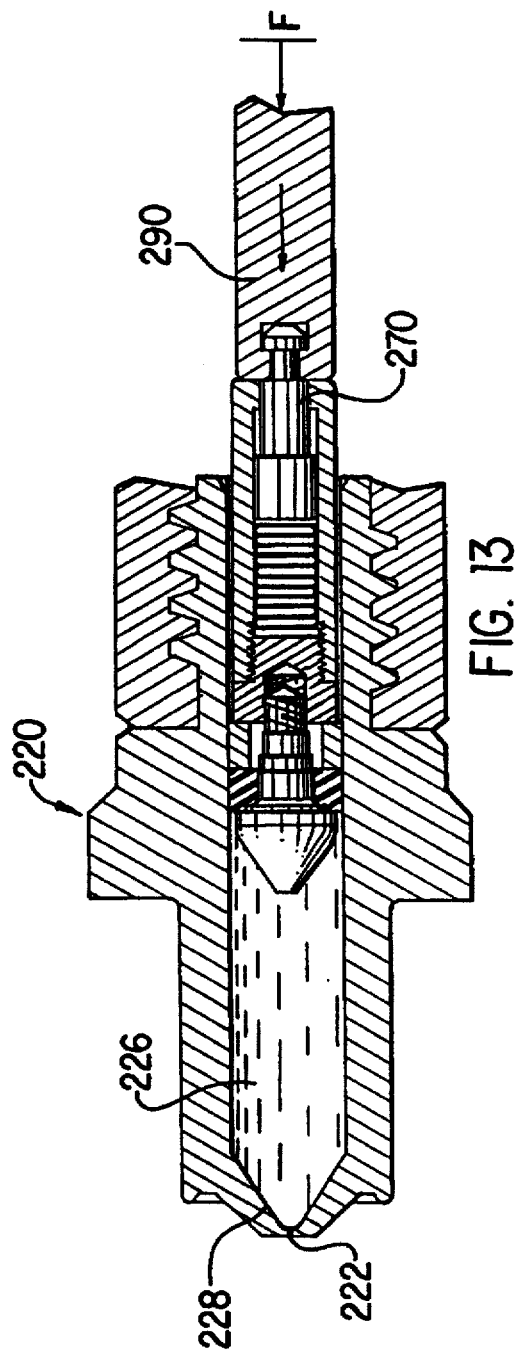
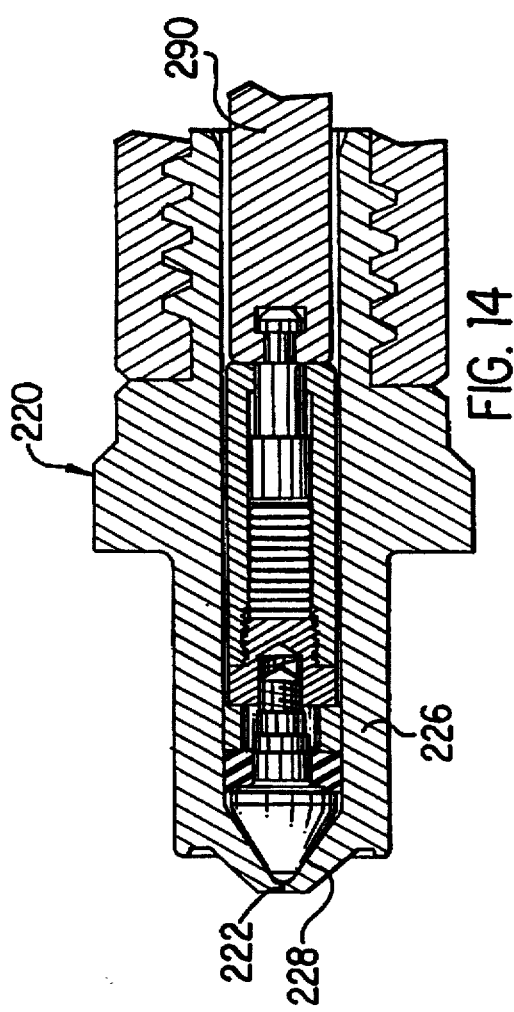
FIG. 13
FIG. 14

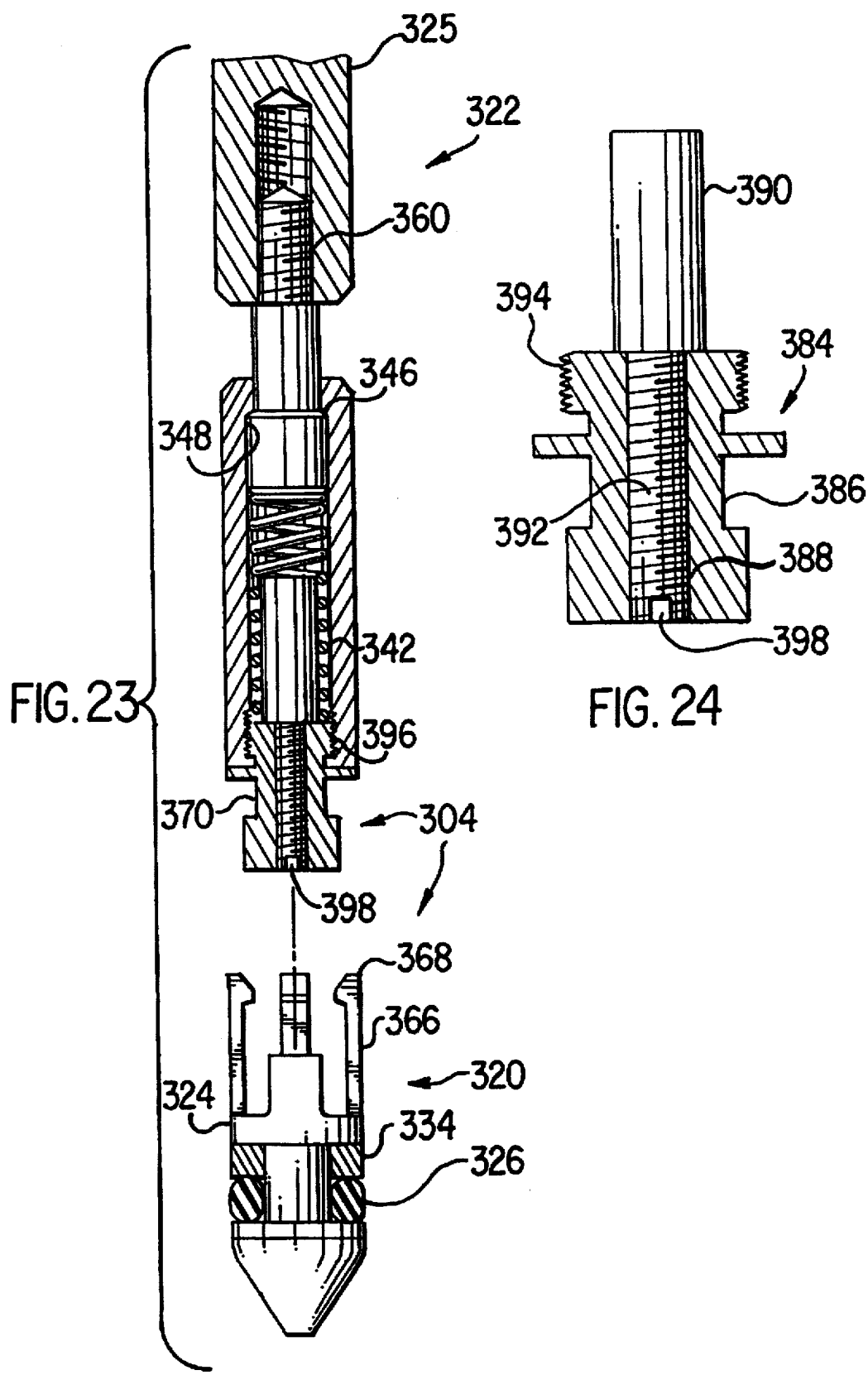

NOZZLE ASSEMBLY WITH ADJUSTABLE PLUNGER TRAVEL GAP

TECHNICAL FIELD

The present invention relates to a fluid injector nozzle assembly having a plunger which includes first and second driving members which are spaced by a predetermined travel distance representative of the injection force. This travel distance is selectively adjustable by the user's choice of plunger mechanisms or by internal mechanisms which can be manipulated to vary the travel distance.

BACKGROUND

Medical communities have become concerned over the possibility of accidental communication of disease, such as Acquired Immune Deficiency Syndrome (AIDS), hepatitis, and other diseases communicable through bodily fluids, through accidental needle sticking and improperly sterilized multiple-use needle injector. One way to curb some of these mishaps is to discard the entire needle injector after a single use.

A number of single use needle injectors have been contemplated in this regard, as described in U.S. Pat. Nos. 5,226,882 to Bates; U.S. Pat. No. 5,423,756 to van der Merwe; U.S. Pat. No. 5,135,507 to Haber et al; and U.S. Pat. No. 5,407,431 to Botich et al. As with all needle injectors, they provide a barrel for holding medication and a plunger/piston assembly slidingly received within the barrel for ejecting medication out of the barrel. The Bates and van der Merwe patents disclose a piston (the forefront part that pushes medication) that separates from a plunger (the rod-like portion that pushes the piston) after medication is ejected. The Haber and Botich patents achieves a similar result by locking the piston to the barrel after the injection stroke is completed to prevent reuse. Needleless injectors have no needle. They thus completely remove any apprehension or the possibility of being pierced. At least in this regard, the needleless injectors are superior in eliminating accidental disease transmission. Different needleless injector types have been contemplated, as described, for instance, in U.S. Pat. No. 5,062,830 issued to Dunlap; U.S. Pat. No. 4,790,824 to Morrow et al.; U.S. Pat. No. 4,623,332 to Lindmayer et al.; U.S. Pat. No. 4,421,508 to Cohen; U.S. Pat. No. 4,089,334 to Schwebel et al.; U.S. Pat. No. 3,688,765 to Gasaway; U.S. Pat. No. 3,115,133 to Morando; U.S. Pat. No. 2,816,543 to Venditty et al.; and U.S. Pat. No. 2,754,818 to Scherer. These injectors have been contemplated to administer medication as a fine, high velocity jet, delivered under sufficient pressure to enable the jet to pass through the skin tissue without requiring a hypodermic needle. These injectors typically have a nozzle assembly which has a barrel-like nozzle body for holding medication therein. The nozzle member has an orifice through which a jet stream of medication is forced out from the chamber when a plunger/piston is actuated by an energy source, such as a coil spring, gas spring, and gas cartridge.

Even though needleless injectors eliminate known problems associated with the needle injector type, nevertheless, as an added safety precaution, it would be desirable to discard the nozzle assembly after each use to prevent its reuse. For example, after a single use the high pressure applied by the energy source may cause the seal between the plunger/piston and the nozzle assembly to partially fail or leak. Thereafter, a subsequent use of the same nozzle may have inadequate pressure transmitted to the medication to ensure proper delivery. Additionally, this high pressure may enlarge the orifice in the nozzle assembly so that subsequent uses of the same assembly would not produce a jet having sufficient velocity to penetrate to a desired depth.

In addition, some of these devices include rather complicated mechanisms for filling and bleeding of the fluid chamber, and cannot accurately control the delivery force which is applied to eject the fluid out of the chamber. The present invention provides new constructions which possess improvements in these areas.

SUMMARY

The present invention relates to a nozzle assembly adapted for use with an injector device having an energy generating source and a chamber adapted for holding a fluid and having first and second end portions with an orifice defined at the first end portion for passage of the fluid and being open at the second end portion. The device includes a first driving member movably positioned in the chamber; a second driving member movably positioned in the chamber and spaced apart from the first driving member according to a predetermined travel distance and including an end portion operative for expelling fluid out of or drawing fluid into the chamber via the orifice; and a spacing member disposed between the first and second driving members for maintaining said predetermined travel distance during displacement of the first and second driving members before the energy generating source is activated.

In one embodiment, the spacing member comprises a frangible connection between the first and second driving members, wherein when the energy generating source is activated, it produces a force upon the second driving member sufficient to break the frangible connection and to drive the second driving member across said predetermined travel distance toward the first driving member for urging the first driving member towards the chamber orifice to expel fluid therefrom. The first driving member typically includes a seal member to prevent fluid from exiting the chamber around the first driving member and through the open end, while the frangible connection preferably has a smaller cross-sectional area than either of the first and second driving members.

The second driving member may include an end post which can be grasped to move the second driving member in a direction away from the chamber orifice to either draw fluid into the chamber or to remove the second driving member from the chamber, and wherein, after firing, the first driving member remains in the chamber to prevent reuse of the nozzle assembly. Advantageously, the first and second driving members are manufactured with indicia representative of a predetermined travel distance, so that different travel distances can be provided by selection of first and second driving members having different indicia. These indicia can include a specific color code, selected from different color codes, corresponding to a respective predetermined travel distance between the first and second driving members.

The chamber preferably includes a tapered portion adjacent the orifice and the second driving member includes a tapered cone which conforms to the tapered portion of the chamber. The first and second driving members may be cylindrical and have D-shaped end portions which face each other with the frangible connection comprising a rectangular bridge connecting straight sides of the D-shaped portions.

In another embodiment, the spacing member comprises a resilient biasing member disposed between the first and second driving members for resiliently maintaining said predetermined travel distance. The resilient biasing member may be a spring, with the first and second driving members operatively connected by a sleeve member and the spring being disposed within the sleeve member between the driving members. The first driving member can have a seal in contact with an inner wall of the chamber to prevent fluid from exiting the chamber around the first driving member and through the open end. The chamber generally includes a tapered portion adjacent the orifice and the first driving member includes a tapered cone which conforms to the tapered portion of the chamber.

In another embodiment, the resilient biasing member has a preselected preload and is operatively disposed for maintaining the predetermined travel distance when the preload is greater than a movement force applied to the second driving member. Also, the first driving member can include a plunger which is removably connected at the forward end thereof for expelling fluid from the chamber orifice. This allows the nozzle assembly to be disposed of after each use. In this construction, the plunger can include a first end portion facing the first driving member and a second end portion adapted to face the orifice of the chamber. Also, the first driving member can include a first end portion facing the second driving member and a second end portion facing the first end portion of the plunger, with the first end portion of the plunger and the second end portion of the first driving member including releasable engagement means which form the removable connection.

The releasable engagement means may be adapted to cooperate with the chamber so as to be maintained in an engaged state when the nozzle assembly is positioned within the chamber, and can be disengaged only when removed from the chamber. Thus, the device can be used without concern of accidental disengagement of the nozzle assembly. The first driving member can include a tail portion facing the second driving member and having a preselected length which controls the predetermined travel distance. The tail portion of the first driving member has an adjustable length to selectively vary the predetermined travel distance.

Another embodiment of the invention relates to a nozzle assembly adapted for a needleless hypodermic fluid injector having a ram and a nozzle member defining a blind bore with at least one orifice communicating with the bore. This nozzle assembly includes a first driving member; a second driving member selectively spaced apart from the first driving member according to a free travel distance; and a plunger member adapted to be movably positioned within the bore. The bore and movable plunger member collectively define a variable-volume fluid chamber communicating with the orifice, with the plunger member adapted to be selectively movable by the ram between a first position at which the fluid chamber has a minimum volume, a second position at which the fluid chamber has a maximum volume, and an intermediate position at which the fluid chamber has an intermediate volume smaller than the maximum volume and greater than the minimum volume.

The second driving member is spaced apart from the first driving member by a preselected free travel distance, and the plunger member and first and second driving members are operatively connected to each other for selectively expelling fluid from and drawing fluid into the chamber. The device also includes a member operative for maintaining the predetermined travel distance when the plunger assembly is moved from its second position to its intermediate position and for collapsing the predetermined travel distance when the plunger assembly is moved from its intermediate position to its first position. Advantageously, the plunger member is removably connected to the second driving member and is disposable.

Another aspect of the invention is an injection device comprising a housing, an energy source, a trigger mechanism for activating the energy source and one of the nozzle assemblies described above, with the nozzle assembly being removably attached to the housing for disposal after each use.

BRIEF DESCRIPTION OF THE DRAWINGS

A better understanding of the invention may be obtained from a review of the appended drawing figures, which illustrate preferred embodiments and wherein:

FIG. 6 is a partial cross-sectional view of a nozzle assembly according to the present invention adapted to be connected to an injector only partially shown;

FIG. 7 is a partial cross-sectional view of a plunger assembly according to the present invention adapted to be connected to a ram only partially shown;

FIG. 8 is a partial cross-sectional view of a tip member of the plunger assembly shown in FIG. 7;

FIG. 9 is a cross-sectional view of the sleeve member of the plunger assembly shown in FIG. 7;

FIG. 10 is an external view of a pin member of the plunger assembly shown in FIG. 7;

FIG. 11 is a partial cross-sectional view of the nozzle assembly of the present invention after drawing fluid into a chamber;

FIG. 12 is a partial cross-sectional view of the nozzle assembly of the present invention ejecting air and/or excess fluid out of the chamber;

FIG. 13 is a partial cross-sectional view of the nozzle assembly of the present invention after the energy device has been activated and the ram has traveled across a predetermined gap;

FIG. 14 is a partial cross-sectional view of the nozzle assembly of the present invention after the plunger has pushed the fluid out of the chamber.

FIG. 23 is a diagrammatic exploded cross-sectional view of a second embodiment of a plunger/ram assembly of the present invention.

FIG. 24 is a diagrammatic isolated enlarged partial cross-sectional view of an adjustable tip or first driving member shown in FIG. 23.

DETAILED DESCRIPTION OF THE DRAWINGS

Figure 1:
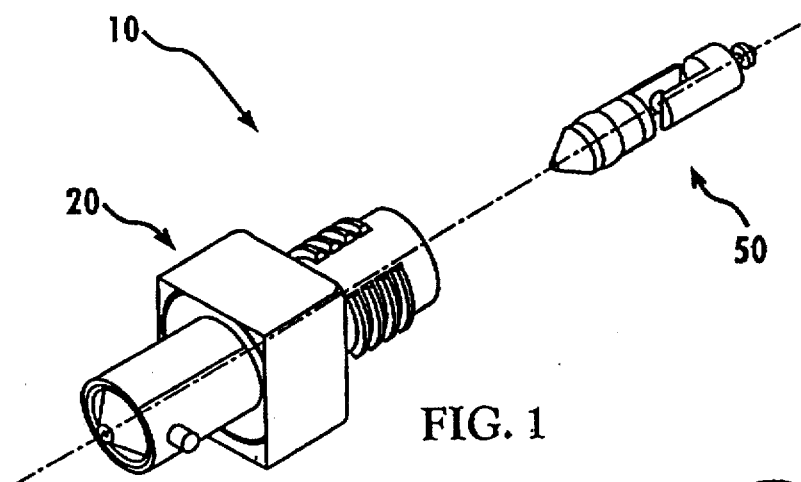
FIG. 1 is an exploded perspective view of a nozzle assembly according to the present invention.

The nozzle assemblies of the present invention are adapted for use with any conventional injector, including the needleless type disclosed in the aforementioned patents, the disclosure of which is incorporated herein by reference. When a needle type injector is to be used, the orifice is in fluid communication with the bore of an appropriately sized needle.

The nozzle assembly has a nozzle member which includes an orifice of a suitable diameter that would produce a uniform jet stream under a given desired pressure range and depth of injection. Preferably, this diameter may be about 0.07–0.4 mm, and most preferably about 0.165 mm (0.0065 inches). If a highly precise jet stream is desired, the orifice can be formed of a synthetic gem material, such as a synthetic ruby or sapphire, as disclosed in U.S. Pat. No. 4,722,728 to Dixon. Hereinafter, the term "orifice" shall mean any type of opening, including a straight, convergent, divergent, convergent-divergent, etc.

The orifice may also be used to withdraw a fluid or liquid medication into the chamber. In this regard, a medication filling device such as an adapter for filling the internal chamber of a nozzle assembly from a liquid medication supply vial directly through the ejection orifice can be used to fill the chamber with medication, as described in U.S. Pat. No. 4,507,113 to Dunlap; and U.S. Pat. No. 4,883,483 and U.S. Pat. No. 4,662,878 to Lindmayer, the disclosure of which is incorporated herein by reference. Other coupling devices can also be used if desired.

In one embodiment of the invention, the predetermined travel distance is provided by a frangible plunger mechanism which maintains the travel distance between two halves of the plunger which are separated by a frangible connection member. This embodiment is shown in FIGS. 1–5.

This nozzle assembly 10 includes a nozzle member 20, as shown in FIGS. 5A–5E, having a cylindrical ampule chamber 26 terminating in a right circular cone 28. The chamber includes external ridges 40 for attachment to an injection device. The plunger 50 has a pressure wall contoured to the cone 28 and is received through an open end of the chamber. It is positioned to slide longitudinally within the ampule chamber 26 to expel fluid medication out of the chamber and may also draw fluid medication into the chamber.

Figure 4:
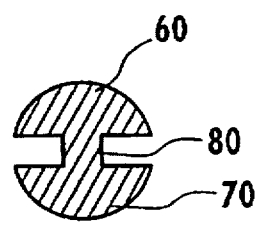
FIG. 4 is a cross sectional view taken along line 4—4 of FIG. 2.
Figure 2:
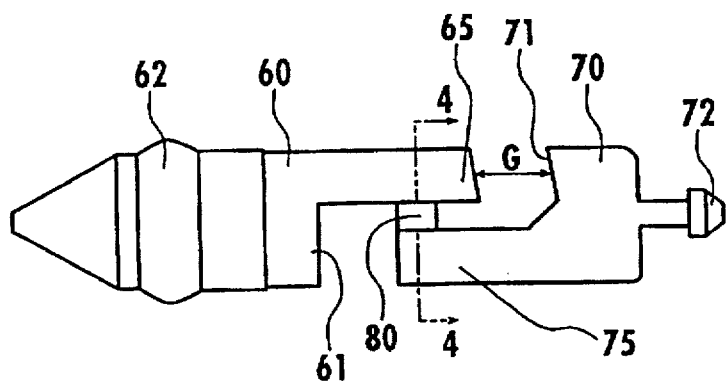
FIG. 2 is an elevational view of a frangible plunger according to the present invention, showing the plunger before injection.
Figure 3:
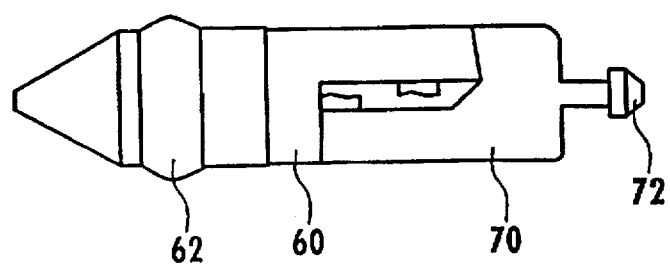
FIG. 3 is a view similar to FIG. 2, but with the plunger during or after injection.

As better shown in FIGS. 2 and 3, this plunger 50 is frangible and has a first driving member 60 and a second driving member 70. As shown, these members have a generally cylindrical shape with D-shaped end portions 65, 75. These driving members are connected together in a spaced apart relationship across a predetermined travel distance or gap G by a frangible connection or bridge 80. As shown in FIG. 4, the preferred frangible bridge 80 is a relatively thin rectangular member connecting the D-shaped end portion of the first driving member 60 to that of the second driving member 70. Advantageously, the frangible bridge 80 has a square cross-section. The frangible bridge 80 may be disposed in a perpendicular position to both straight sides of the D-shaped end portions 65, 75 of the first and second driving members as well as to the longitudinal axis of the first 60 and the second 70 driving members, which are parallel to the longitudinal axis (direction of the sliding movement) of the plunger 50. Preferably, the plunger 50, including the frangible bridge 80 is made out of a plastic, such as polycarbonate or polypropylene and is configured and dimensioned such that frangible bridge 80 can withstand a force "p" for moving or withdrawing the plunger to draw liquid medication into ampule 26 without breaking.

Alternatively, the frangible plunger 50 can be used with a prefilled ampule, thereby eliminating the need for moving the plunger longitudinally to draw liquid medication into ampule 26 or to expel excess liquid or bubbles therefrom.

The leading end of the first driving member 60 includes a seal 62, such as O-ring or the like, preferably formed around its outer periphery to provide a seal with the inner wall of the chamber. The plunger 50 itself can be a seal. Other seals or seal members can be included in the trailing end of the second driving member if desired to provide a better seal to prevent leakage of fluid for the chamber by minimizing the entry of air into the chamber from around the first 60 and second 70 driving member and by preventing air from entering the orifice 22 due to liquid exiting the chamber 26 around the driving members 60, 70.

Figure 5A:
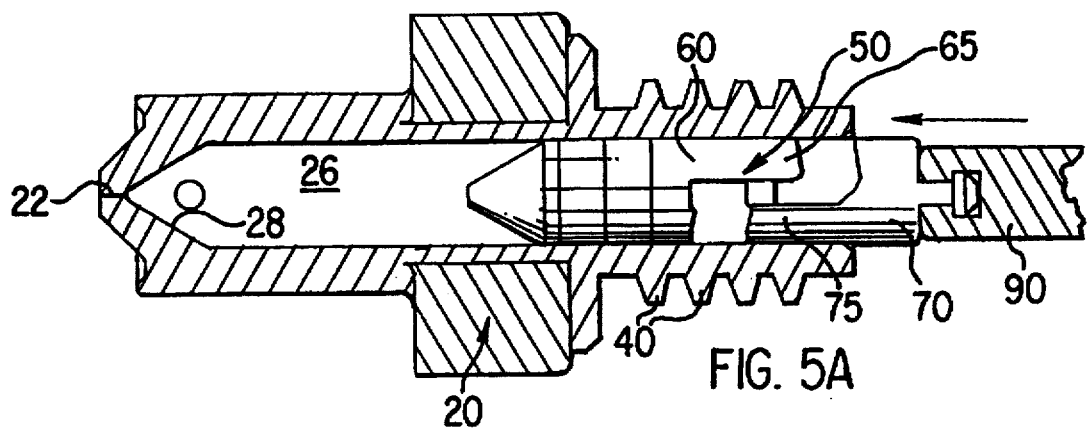
FIG. 5A is a cross-sectional view of the present nozzle assembly with the plunger pulled away from the nozzle member.

Referring to FIGS. 5A–5E, the nozzle assembly 10 is attached to an injector body by connecting the end post 72 of the second driving member 70 to the ram 90 of the injector, as shown in FIG. 5A, and connecting the bayonet mount 40 to the front of the injector body (not shown). The connection between the plunger 50 and the ram 90 can be any conventional connection that holds these elements together but enables separation, such as a ball and slot configuration as depicted.

Figure 5B:
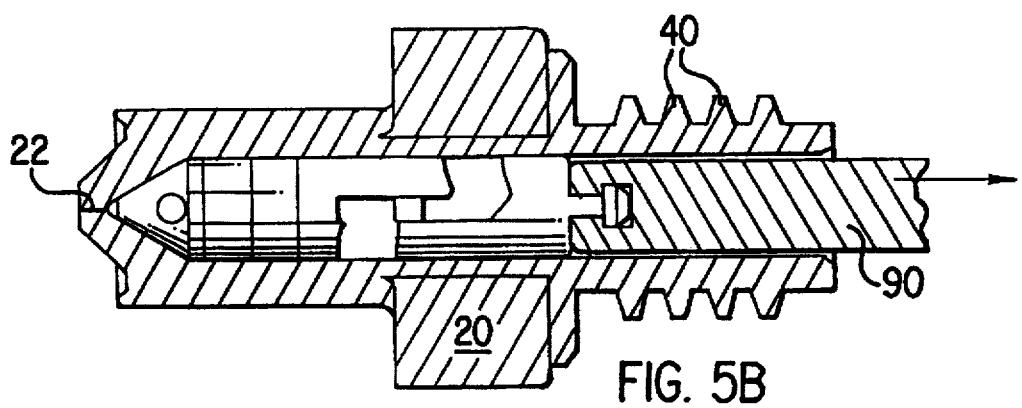
FIG. 5B is a cross-sectional view of the present nozzle assembly before withdrawing medication into the ampule chamber.
Figure 5C:
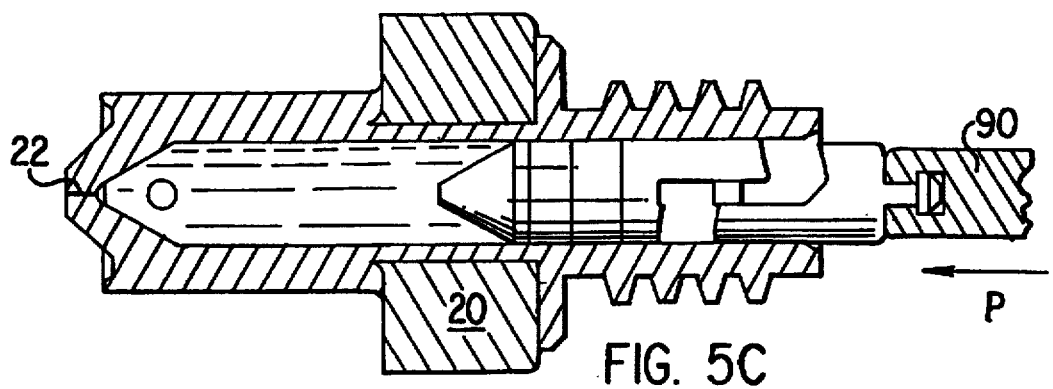
FIG. 5C is a view of the injector of the present injector after medication has been introduced into the barrel of the injector.

The plunger 50 is pushed into the chamber 26, in the direction shown by the arrow in FIG. 5A, to purge air. FIG. 5B shows the plunger 50 fully pushed, before the liquid medication is drawn into the chamber 26. As the plunger 50 is pulled to the direction shown by the arrow in FIG. 5B, a partial vacuum is established inside the chamber 26 and liquid medication is drawn into the chamber 26 through the orifice 22.

Figure 5D:
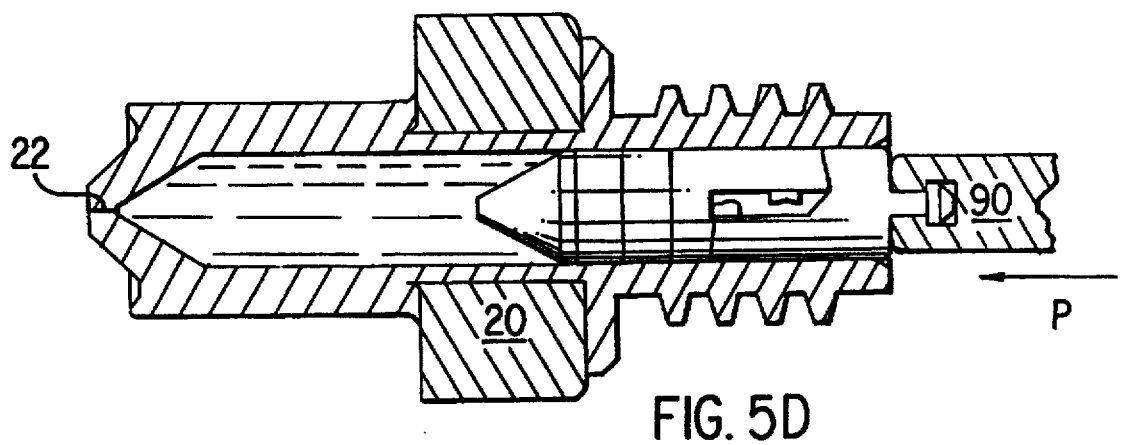
FIG. 5D is a view of the injector of the present invention after the frangible member of the piston is broken.
Figure 5E:
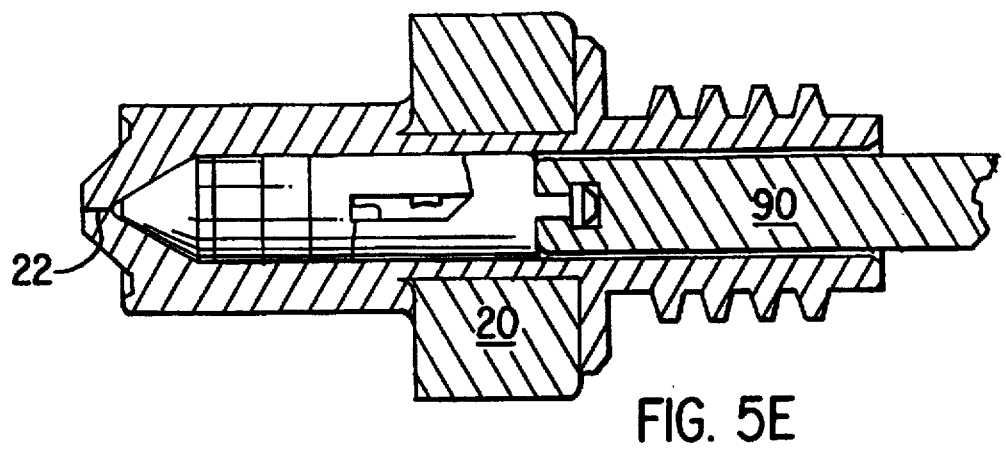
FIG. 5E is a view of the injector of the present invention after the piston has pushed the liquid out of the barrel.

It will be noted that the frangible connection is dimensioned and configured such that pushing or pulling action requiring force "p" normally affiliated with withdrawal and slow ejection of air or medication before injection does not break the bridge 80. Upon an application of a relatively large injection force "P" on the ram 90, which may be significantly larger than the force "p", the ram 90 transmits this force P to the second driving member 70 and breaks the frangible bridge 80. This allows the second driving member 70 to close the gap G and transmit force to the first driving member 60 to eject medication out of the chamber 26, as shown in FIG. 5D. Finally, FIG. 5E shows the position where the injection is completed and all the medication has been ejected. At this point, the nozzle assembly 10 can be rotated until the ridges 40 are free of the injection device and it can be removed. Since the first driving member 60 is broken away from the second driving member 70, which remains connected to the ram 90, the first driving member 60 remains inside the chamber 26. The second driving member 70 is then removed from the ram 90 and discarded along with the nozzle assembly 10. This prevents unwanted re-use of the nozzle assembly 10.

In a normal operation of the injector, ram 90 of the injection device, operatively connected to an energy source, imparts sudden force or impact P to the second driving member 70, enough to drive the second member 70 into the first member 60. This action is sufficient to drive the liquid contained in ampule 26 outward through orifice 22 at a peak jet stream pressure, for example, in excess of 5,000 psi out of the orifice 22. This sudden force is capable of breaking the frangible bridge 80 before the injection begins. Specifically, the force P applied to the second driving member 70 is transmitted to the first driving member 60 through the bridge 80. Initially, the frictional force in the seal 62 generates enough friction to momentarily prevent the plunger 50 from moving. Once this frictional force is overcome, the plunger starts to move and imparts pressure to the medication in the chamber. This creates resistance or back pressure on the first driving member. When the difference between the resistance force imparted to first driving member 60 by the fluid and the force imparted by the second driving member 70 toward the first driving member 60 reaches a predetermined level, the bridge 80 breaks and the second driving member 70 rams into the first driving member 60.

Alternatively, frangible bridge 80 may be broken by an intermediate force larger than the force p, before the relatively large injection force P is applied on ram 90. Such an intermediate force can be generated for example by a pressure exerted on the liquid contained in ampule chamber 26 through orifice 22 or by other triggering mechanism.

The gap G plays an important role in creating a preferred pressure spike necessary to pierce through the patient's skin. Changing the gap G will change the initial force imparted on the first driving member. The peak pressure thus can be varied with the gap G. It can also vary depending upon the viscosity of the medication, the desired injection penetration depth and other parameters which may affect the initial injection pressure output. One of ordinary skill in the art can determine by routine experimentation the optimum gap for any frangible plunger 50 that is to be used with a particular medication. Advantageously, frangible plunger 50 or nozzle assembly 10 or both can be manufactured with different colors, wherein each color denotes a predetermined width of gap G. This color coding scheme will assist the user in choosing a proper nozzle assembly for a specific application.

Once the first 60 and second 70 driving members are separated, the first driving member 60 remains stuck in the chamber. The chamber and the plunger 50 thus becomes unusable. The amount of force to break the gap can be adjusted by changing the dimension of the bridge 80. Additionally, scoring lines or lines of breakage can be provided to controllably break the bridge 80. These can also be determined by routine experimentation to optimum performance criteria.

The nozzle assembly 10 can be connected to an injection device using any known structure for attaching and detaching two components together. The present invention preferably contemplates a bayonet-mount, which has diametrically opposed ridges 40. These ridges 40 are first aligned in an opening having a similar cross-sectional configuration provided in an injector so that the ridges can be inserted. Thereafter, the nozzle member 20 is rotated relative to the injector body by a predetermined degree to prevent the nozzle body from detaching in the axial direction. The bayonet-mount enables a quick attachment and detachment of the nozzle assembly 10. Alternatively, threads can be used to secure the nozzle assembly 10 to the injection device. Other connection means can be used, if desired for a particular application.

It will be understood that the frangible plunger 50 according to the present invention can also be used with syringes having hypodermic needles where the frangible bridge 80 breaks either before the injection begins or after the completion of the injection.

In another embodiment of the invention, as shown in FIGS. 6–14, the nozzle assembly 210 has a nozzle member 220, which includes a cylindrical ampule chamber 226 terminating in a right circular cone 228. The chamber 226 includes external helical threads 240 for selectively removable attachment to an injection device. The plunger assembly 250, as shown individually in FIG. 7, has a pressure wall contoured to the cone 228 and is received through an open end of the chamber 226. It is positioned to reciprocally move longitudinally within the ampule chamber 226 to expel fluid out of the chamber and may also draw fluid into the chamber.

As better shown in FIGS. 7–10, plunger assembly 250 comprises a tip member or first driving member 260, a pin member 270, a sleeve member 280, and a resilient spring member 282. These members have a generally cylindrical shape and are connected together as shown in FIG. 7. Preferably, the spring member 282 is a helical compression spring. Pin member 270 as shown in FIGS. 7, 9 and 10, is inserted into sleeve member 280 until an external annular shoulder 274 of the pin member 270 comes into contact with an internal annular shoulder 281 of the sleeve member 280. The relative sizes and orientations of the shoulders 274, 281 help ensure that the pin member 270 is retained within the sleeve member 280. An end post 272 of the pin member 270 extends outside of sleeve member 280. Spring 282 is then inserted into sleeve member 280 as shown. Finally, tip member 260 is threadedly connected to sleeve member 280, and compresses spring member 282 to a point where a predetermined first distance $D_1$ or spacing between the distal end of tip member 262 and the proximal end of pin member 270 is resiliently maintained.

Referring to FIG. 8 tip member 260 comprises front member 262, which has a conical head or tapered pressure wall member 263, a connecting member 264, and a back member 266. Alternatively, the back member 264 may be integrally formed with the front member 262. A seal member 267 and adjacent backup ring 268 are disposed between front member 262 and back member 266. As shown in FIG. 6, seal member 267 is preferably an O-ring having an outer diameter which is slightly larger than the inner diameter of ampule member 226, so that plunger assembly 250 is in a slidingly sealing relationship with ampule chamber 226.

As shown in FIG. 8, the connecting member 264 of front member 262 is threadedly connected to back member 266. In this configuration, when seal member 267 has to be replaced, front member 262 can be separated from back member 266 to expose seal member 267 for removal and replacement. Furthermore, back member 266 comprises tail member 269, which is received within spring member 282. As stated above, the distance between the distal end of tail member 269 and the proximal end of pin member 270 constitutes the first distance $D_1$. Conical member 263 is configured and dimensioned to fit within cone 228 so that when plunger assembly 50 is pushed against ampule chamber 226, substantially all the fluid is expelled from ampule chamber 226.

Preferably, the plunger assembly 250 is made out of a plastic, such as polycarbonate or polypropylene, or a more durable material such as aluminum, stainless steel, or other metal. As described above, members of the plunger assembly 250 can be easily separated for cleaning or replacement.

Referring to FIGS. 6 and 11-14, the nozzle assembly 210 is attached to an injector body by connecting the end post 272 of the pin member 270 to the ram 290 of the injector, and connecting the external helical threads 240 to the complementary internal helical threads 292 defined in a front portion of the injector body 294. The connection between the plunger assembly and the ram 290 can be any conventional connection that holds these elements together but enables separation, such as a ball and slot configuration as depicted. The distal end 284 of the sleeve member 280 and the proximal end 292 of the ram 290 are spaced apart according to a predetermined second distance $D_2$ which is preferably selected to be smaller than the first distance $D_1$. Thus, the second distance $D_2$ constitutes the controlled gap or free travel distance that the ram 290 travels before impacting or otherwise moving the distal end of the sleeve member 280. In this embodiment, the sleeve member 280 functions as a second driving member. The relatively large surface area of the annular distal end 284 of the sleeve member 280 advantageously accommodates the impact loading by the ram 290 and resists wear from repeated use of the injector.

The plunger assembly 250 is pushed proximally into the ampule chamber 226, to purge air. FIG. 6 shows the plunger assembly 250 fully pushed, before the desired injection fluid is drawn into the chamber 226. As the plunger assembly 250 is pulled distally, a partial vacuum is established inside the chamber 226 and the desired fluid is drawn into the chamber via the orifice 222, as depicted in FIG. 11.

In the event that air bubbles and/or excess fluid are drawn into ampule chamber 226, the plunger assembly 250 must be pushed distally proximally to expel the bubbles or excess fluid. As shown in FIGS. 11 and 12, and according to a preferred embodiment of the present invention, spring member 282 has sufficient stiffness to resist relative movement between pin member 270 and tip member 260. And since spring member 282 is pre-loaded (being compressed within sleeve member 280), any slight relative movement between these two members would be compensated and after the purging process the gap $D_2$ or free travel distance between the ram 290 and sleeve member 280 would be restored. It is within the ordinary skill of the art worker to select a proper resilient spring member to accomplish this purpose. Once installed, the preload on the spring member 282 provides a force greater than the force required to move the plunger assembly 250 within the chamber 26 and towards the orifice 222.

Upon an application of a relatively large injection force F from the injecting device on the ram 290, the ram transmits this force F to the pin member 270. This force F compresses resilient spring member 282 and allows the ram 290 to travel across the gap $D_2$ and directly transmit the force to the sleeve member 280 thereby proximally moving the sleeve member 280 and tip member 260 to eject fluid out of the chamber 226, as shown in FIGS. 13-14. If the nozzle assembly 210 is to be reused by the same patient, the pin member 270 is pulled distally by the ram 290 as depicted in FIG. 11 and, due to the resiliency of the spring member 282, the first and second distances $D_1$, $D_2$ are accurately reestablished or restored.

After fluid injection is completed, the nozzle assembly 210 can be rotated until the threads 240 are free of the corresponding threads 292 on the injector body 294 so that the nozzle assembly 210 can be removed for cleaning and/or replacement of the pin member 270.

In a normal operation of a needleless injector, ram 290 of the injection device is operatively connected to an energy source and imparts a sudden force or impact F to the pin member 270, which force is high enough to compress spring 282 and to allow the ram 290 to directly drive the sleeve member 280 and tip member 260 towards the orifice 222. This action is sufficient to drive the fluid contained in ampule chamber 226 outward through orifice 222 at a relatively high peak jet stream pressure of, for example, in excess of 5,000 psi. By "high pressure", what is meant is a jet stream pressure which is capable of penetrating the skin of a patient. This would be a pressure of greater than 1,000 psi and typically between about 3,000 and 10,000 psi.

The second distance or gap $D_2$ plays an important role in creating the preferred pressure spike necessary to pierce through the patient's skin or other portion of the patient's body. Changing the magnitude of the gap $D_2$ will change the initial force imparted on the tip member 260. The peak pressure thus can be varied by varying the gap $D_2$. It can also vary depending upon the viscosity of the fluid to be injected, the desired injection penetration depth and other parameters which may affect the initial injection pressure output. One of ordinary skill in the art can determine by routine experimentation the optimum gap for any plunger assembly that is to be used with a particular injection fluid. Advantageously, plunger assembly 250 or nozzle assembly 210 or both can be manufactured with different indicia such as different color codes and/or other markings, wherein each different indicia denotes a resulting predetermined length of gap $D_2$. This indicia coding scheme will easily assist the user in choosing a proper nozzle assembly for a specific application.

Also, in another embodiment, the first distance $D_1$ between the distal end 265 of the tip member 260 and the proximal end 276 of the pin member 270 is chosen to be less than the second distance $D_2$. In this arrangement, the pin member 270 functions as the second driving member wherein the proximal end 276 of pin member 270 thrusts into the distal end 265 of tip member 260, when the ram 290 and pin member 270 compress the spring member 282.

The nozzle assembly 210 can be connected to an injection device using any known structure for attaching and detaching two components together. The present invention preferably contemplates a bayonet mount, which has diametrically opposed threads 240. These threads 240 are first aligned in an opening having a similar cross-sectional configuration provided in an injector so that the threads can be inserted. Thereafter, the nozzle member 220 is rotated relative to the injector body by a predetermined degree to prevent the nozzle body from detaching in the axial direction. The bayonet-mount enables a quick attachment and detachment of the nozzle assembly 210. Other connection means can be used, if desired for a particular application.

Additional embodiments are shown in FIGS. 15–32, which illustrate the use of a spring member for maintaining the predetermined travel distance, wherein the distance between the first and second driving members can be varied without substituting different members.

Figure 15:
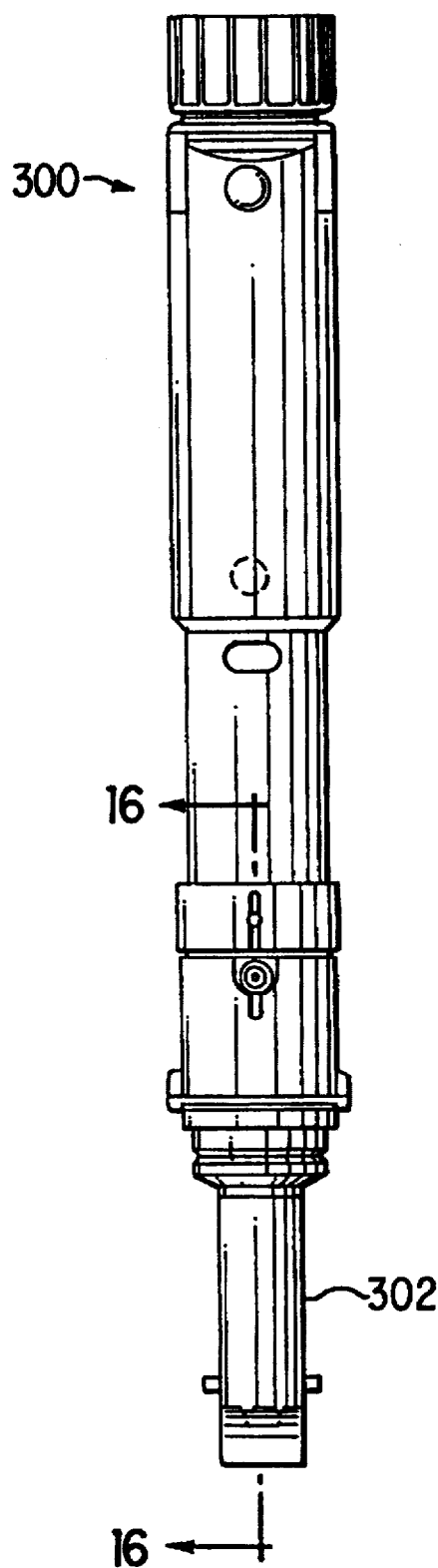
FIG. 15 is a diagrammatic elevational view of a fluid injector including a first embodiment of a plunger/ram assembly of the present invention.
Figure 16:
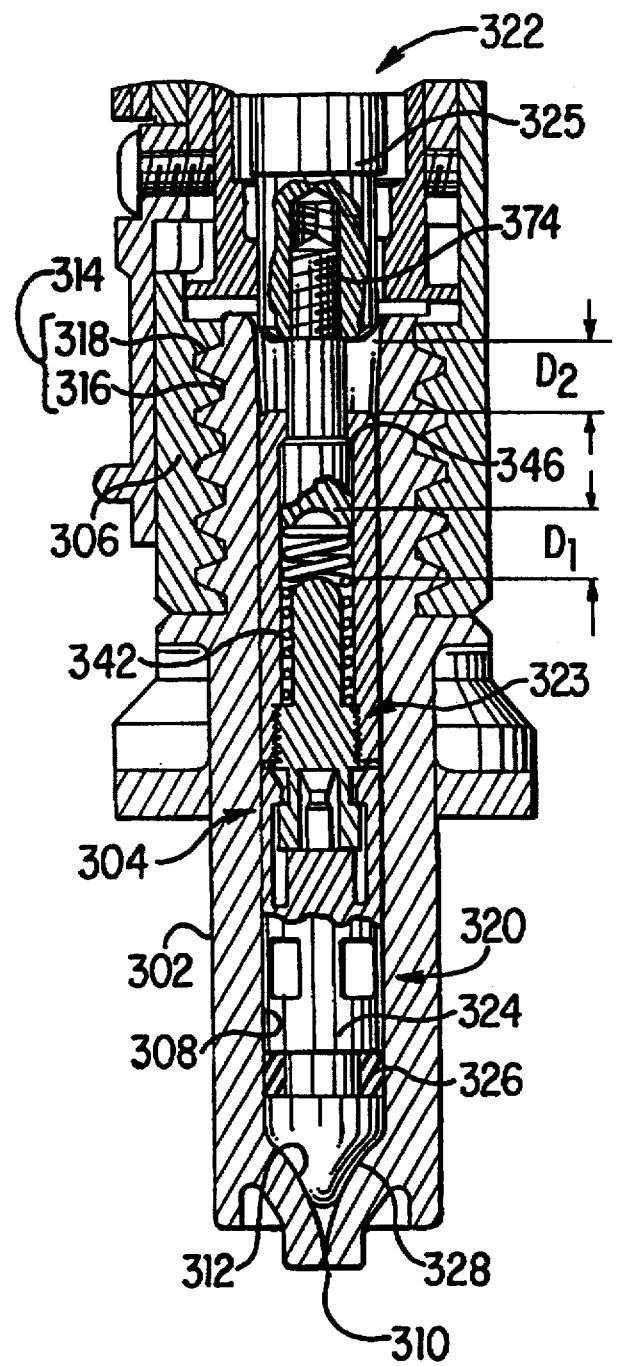
FIG. 16 is a diagrammatic enlarged cross-sectional view of one end portion of the fluid injector taken along line 16—16 of FIG. 15.

In FIGS. 15–16, there is shown a fluid injector 300 having a nozzle body 302, a plunger/ram assembly 304, and an injector housing 306. As shown in FIG. 16, the nozzle body 302 defines a fluid chamber or blind bore 308 and at least one orifice 310 communicating with the chamber. The fluid or ampule chamber 308 has an end portion 312 which is, for example, tapered towards the orifice. The nozzle body 302 and injector housing include connector means 314 for selectively attaching and removing the nozzle body to the injector housing. For example, the connector means 314 may include external helical threads 316 formed around the nozzle body and corresponding internal helical threads 318 formed in the injector housing 306.

The plunger/ram assembly 304 includes a plunger assembly 320 adapted to be movably or reciprocally positioned in the chamber 308 and a ram assembly 322 operatively connected to the plunger assembly for drawing fluid into and drawing fluid out of the chamber 308 through the orifice 310.

The plunger assembly includes a plunger 324 and a seal member 326. The plunger includes a pressure wall 328 contoured to the end portion 312 of the chamber 308 and is received through an open end 330 portion of the chamber. The plunger assembly 304 is positioned to reciprocally move longitudinally within the chamber 308 to expel fluid out of the chamber via the orifice 310 and may also draw fluid into the chamber 308 via the orifice 310.

Figure 17:
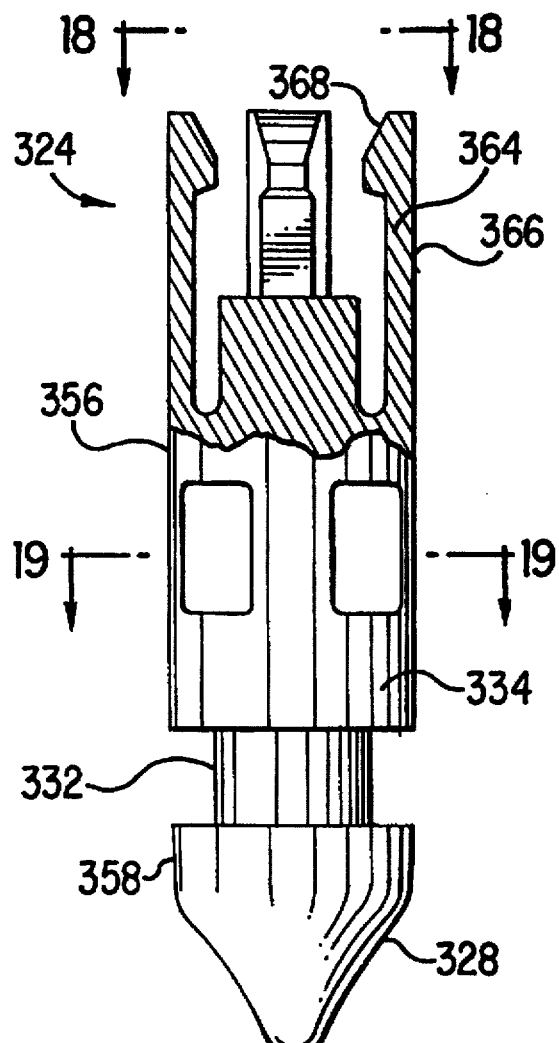
FIG. 17 is a diagrammatic isolated enlarged cross-sectional view of a plunger shown in FIG. 16.
Figure 18:
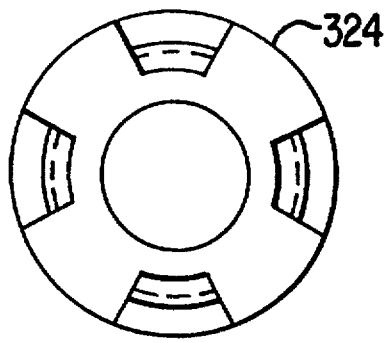
FIG. 18 is a diagrammatic end view of the plunger taken along line 18—18 of FIG. 17.
Figure 19:
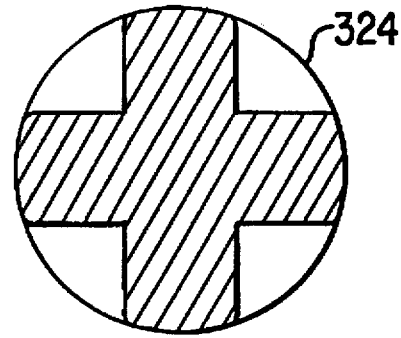
FIG. 19 is a diagrammatic cross-sectional view of the plunger taken along line 19—19 of FIG. 17.

As shown in FIGS. 16 and 17, the seal member is preferably is a separate member such as an o-ring positioned in a circumferential groove 332 defined in the plunger 324. The o-ring has an outer diameter which is slightly larger than the inner diameter of the chamber 308, so that the plunger assembly 320 is in a slidingly sealing relationship with the chamber 308. Alternatively, the seal member 326 may be integrally formed with the plunger such as, for example, selecting a resilient material for the plunger. The plunger assembly 304 may also include a backup ring 334 positioned adjacent to the seal member 326.

As shown in FIGS. 16 and 20–22, the driving members assembly 323 includes a second driving member or pin 336, a first driving member or tip 338, a sleeve 340, and a resilient spring member or biasing member 342. These items have a generally cylindrical shape and are arranged as shown in FIG. 16. The first and second driving members are preferably spaced apart a preselected free travel distance or gap $D_1$. The plunger assembly 324 is connected to the first driving member 338. Preferably, the plunger assembly 320 is removably connected to the first driving member 338 in order to make the plunger assembly 324 disposable.

Preferably, the spring member 342 is a helical compression spring. The pin 336 is inserted into sleeve 340 until an external annular shoulder 346 of the pin 336 comes into contact with an internal annular shoulder 348 of the sleeve 340. The relative sizes and orientations of the shoulders help ensure that the pin is retained within the sleeve. An end portion 350 of the pin 336 extends outside of sleeve 340. The spring 342 is then inserted into sleeve 340 as shown in FIG. 16. Finally, external helical threads 352 of the tip 338 are connected to corresponding internal helical threads 354 of the sleeve 340 which compresses or preloads the spring member 342 to a point where a predetermined first distance $D_1$ or spacing between the distal end 380 of tip (first driving member 338) and the proximal end 378 of the pin (second driving member 336) is resiliently maintained.

Figure 22:
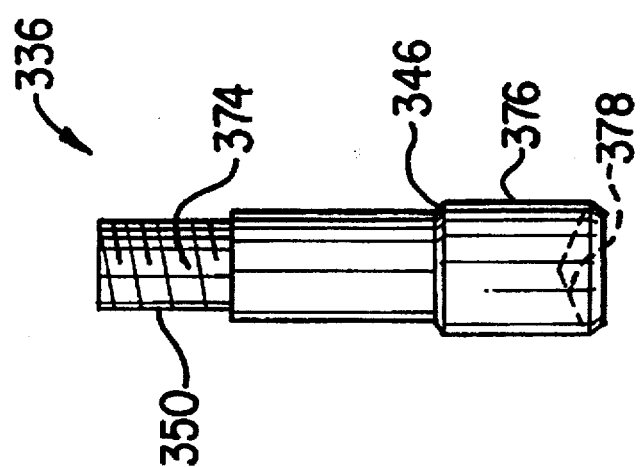
FIG. 22 is a diagrammatic isolated enlarged view of a pin or second driving member shown in FIG. 16.
Figure 21:
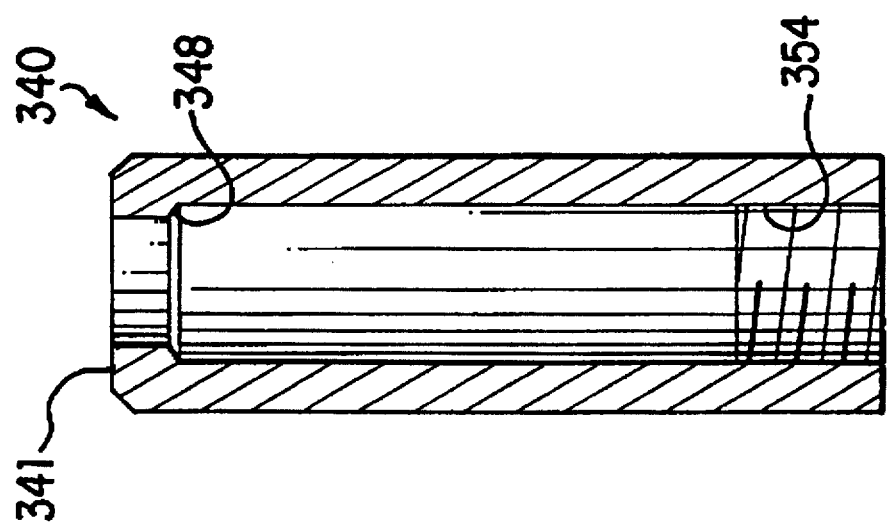
FIG. 21 is a diagrammatic isolated enlarged cross-sectional view of a sleeve shown in FIG. 16.
Figure 20:
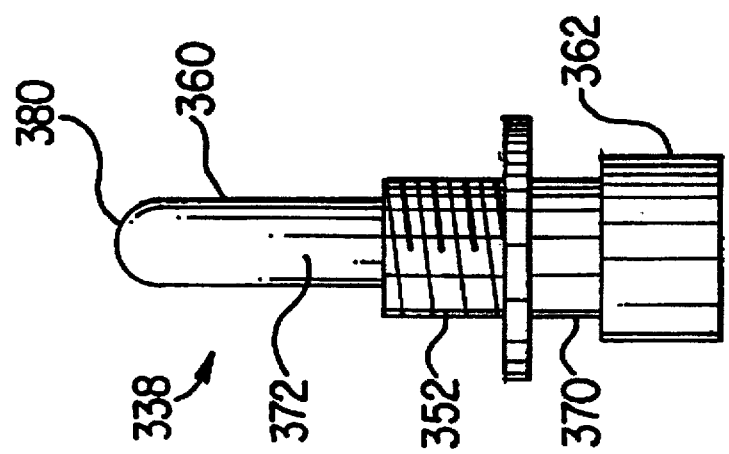
FIG. 20 is a diagrammatic isolated enlarged view of a tip or first driving member shown in FIG. 16.

As shown in FIGS. 16–17, the plunger 324 includes a first end portion 356 facing the first driving member and a second end portion 358 facing the orifice 310 of the chamber 308. As shown in FIGS. 16 and 22, the first driving member or tip 338 includes a second end portion 360, facing the first driving member, and a second end portion 362 facing the first end portion 356 of the disposable plunger 324. The first end portion 356 of the plunger 324 and the second end portion 362 of the tip 338 include releasable engagement means 364 which form a removable connection. As shown in FIGS. 16–17, the plunger 324 preferably includes a plurality of fingers 366 having barbed ends 368 which removably attach to a circumferential groove 370 defined in the tip. The releasable engagement means 364 cooperates with the chamber 308 so as to be maintained in an engaged state when positioned within the chamber. Similarly, the releasable engagement means 364 can be disengaged when it is removed from the chamber 308.

In this configuration, when seal member 326 and/or plunger 324 has to be replaced, the plunger assembly 320 can be separated from tip 338. Furthermore, the tip 338 includes a tail member 372, which is received within the spring member 342. As stated above, the distance between the distal end 380 of the tail member 372 and the proximal end 378 of the pin 336 constitutes the first distance $D_1$.

As shown in FIG. 16, 22 and 23, the second driving member (e.g., pin 336) includes a first end portion 374 adapted to be connected to the ram 325 and a second end portion 376 facing the first end portion 360 of the first driving member 338 (e.g., tip). Preferably, one of the oppositely facing end portions of the first and second driving members has a concave semi-spherical surface 378. The other of the oppositely facing end portions of the first and second driving members preferably has a convex semi-spherical surface 380 which conforms to the concave semi-spherical surface. Thus, the semi-spherical surfaces are resiliently spaced apart by the resilient biasing member 342 according to the free travel distance $D_1$. As compared to planar surfaces, the semi-spherical surfaces advantageously maximize the surface area of impact or contact between the first and second driving members. This minimizes wear and/or deformation between such opposing surfaces after repeated use. Alternatively, the oppositely facing surfaces may be planar or have some other complementary shapes.

Preferably, as in the other embodiments, the plunger assembly 320 may be made out of a plastic, such as polycarbonate or polypropylene, an elastomer, or a more durable material such as aluminum, stainless steel, or other metal.

Referring to FIG. 16, the nozzle body 302 is attached to the injector housing 306 by connecting the external helical threads 316 to the complementary internal helical threads 318 defined in a front portion of the injector housing. The connection between the pin 336 and the ram 325 can be any conventional connection that holds the end portion 374 of the pin 336 to the ram 325, such as the threaded connection depicted. The distal end 341 of the sleeve 340 and the proximal end of the ram 325 are spaced apart according to a predetermined second distance $D_2$ which is preferably selected to be greater than the first distance $D_1$. Thus, the first distance $D_1$ constitutes the controlled gap or free travel distance that the second driving member (e.g., pin 336) travels before impacting or otherwise moving the distal end 380 of the first driving member 338 (e.g., tip). Alternatively, free travel can be set by length $D_2$ being less then $D_1$. In this case, free travel can be adjusted by replacement of the pin 336, the length of which middle portion controls the magnitude of the free travel distance. In other words, the ram 325 will bottom out on sleeve 340.

Figure 25:
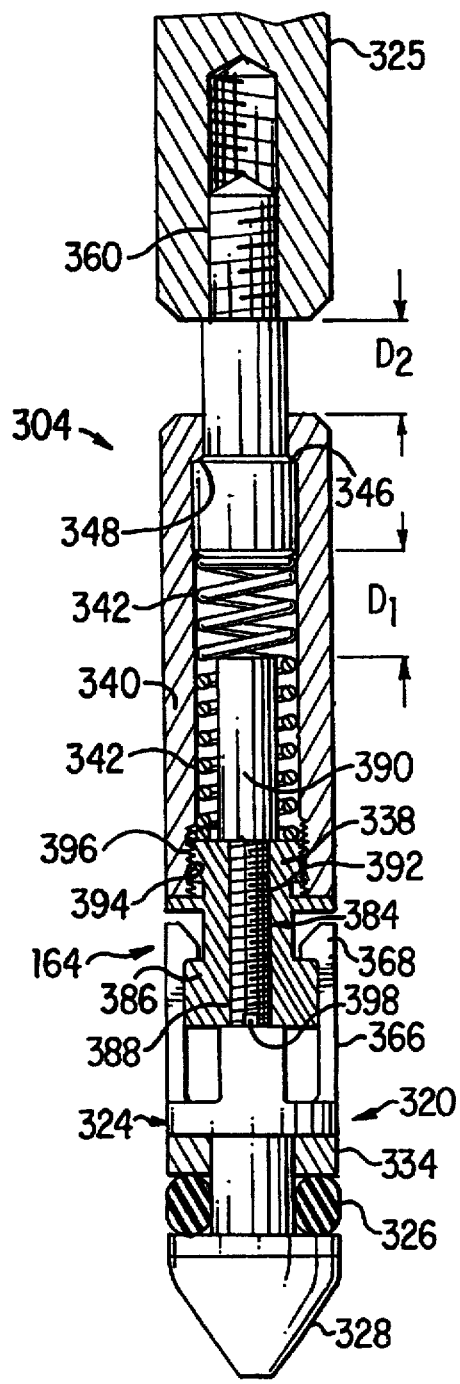
FIG. 25 is a view similar to FIG. 23 but showing the plunger/ram assembly in an assembled state and adjusted for a maximum free travel distance $D_1$.
Figure 26:
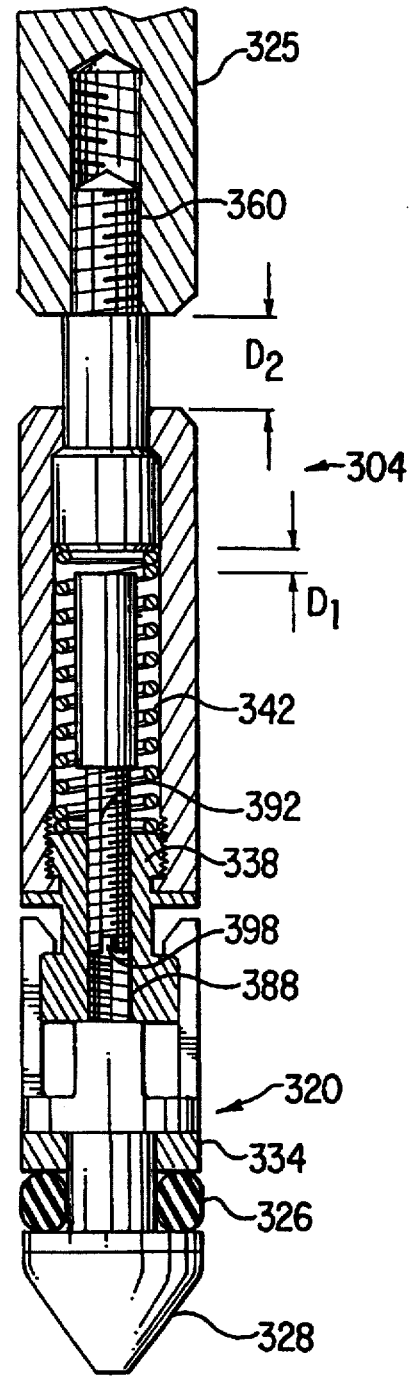
FIG. 26 is a view similar to FIG. 23 but showing the plunger/ram assembly in an assembled state and adjusted for a reduced free travel distance $D_1$.

In the second embodiment shown in FIGS. 25–32, a modified plunger/ram assembly is shown. In this arrangement, the first driving member (e.g., tip 338) has a means 384 for variably adjusting in situ the free travel distance $D_1$. As shown in FIGS. 25–26, the tip 338 includes a bushing 386 having a threaded bore 388 and a tail member 390 having a threaded stem 392 movably positioned in the bore 388 of the bushing 386. The bushing 386 has external helical threads 394 that removably engage corresponding internal helical threads 396 defined on one end portion of the sleeve 340. A free end of the threaded stem 392 has a slot 398 for variably adjusting the effective length of the tail member 390 extending out of the bushing 386. As shown in FIG. 25 shortening the effective length of the tail member 390 increases the free travel distance $D_1$ while lengthening the effective length of the tail member 390 decreases the free travel distance $D_1$.

Figure 27:
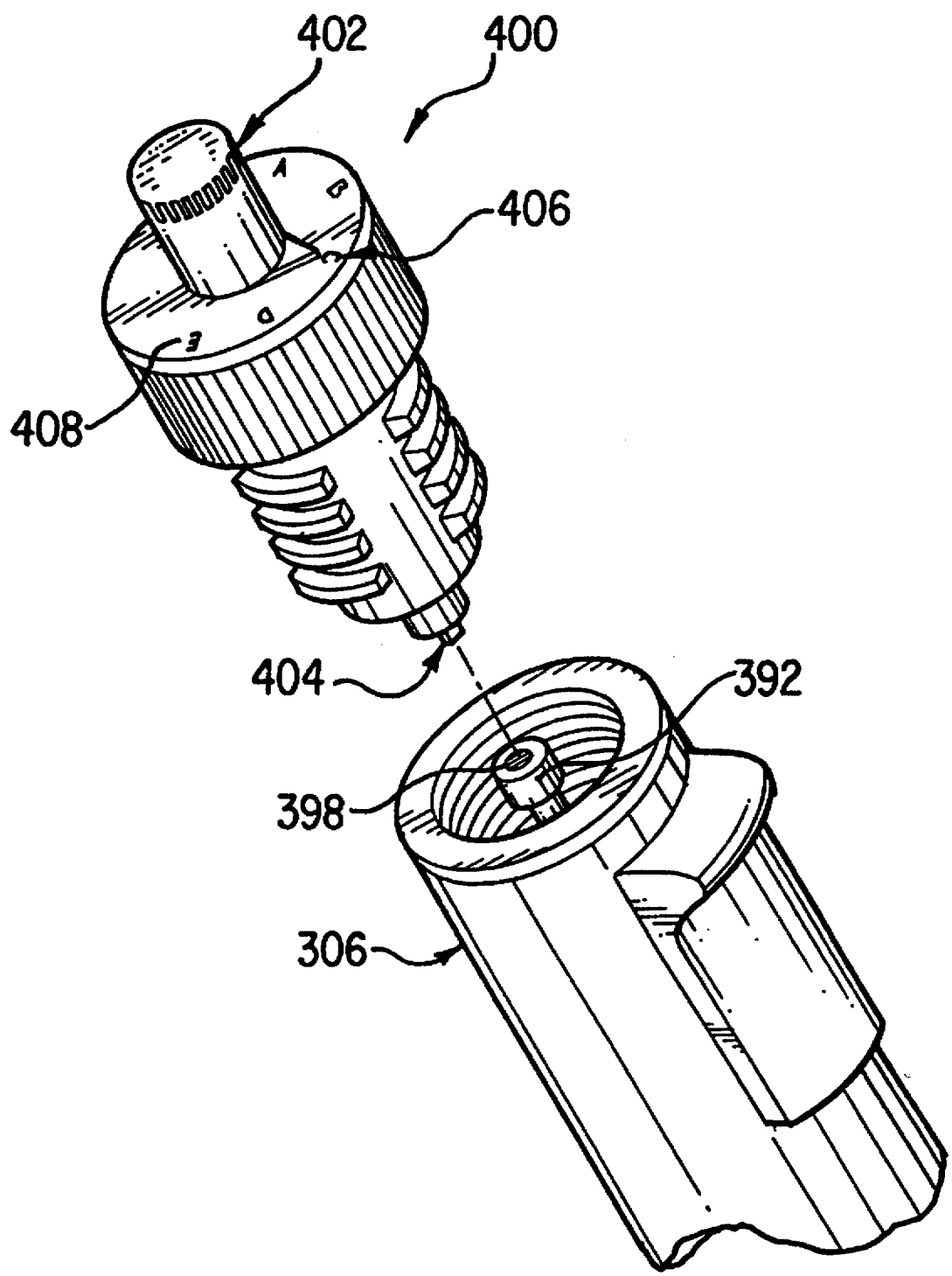
FIG. 27 is a diagrammatic exploded perspective view of an adjustment tool for adjusting the free travel distance $D_1$ of the second embodiment of the plunger/ram assembly, only partially shown.

FIG. 27 shows an adjustment tool 400 for changing the effective length of the tail portion. The adjustment tool preferably includes a knob 402 rotatively connected to a blade 404 adapted to engage the slot 398 of the threaded stem 392. The tool further includes indicator means 406 such as a dial gauge 408 for measuring the displacement or effective length of the tail portion 390 extending outside of the bushing 386 and towards the second driving member.

The plunger/ram assembly according to the present invention is adapted for use with any fluid injector, including the hypodermic fluid injectors disclosed in the aforementioned patents, the disclosure of which is incorporated herein by reference. When a needle-type injector is to be used, the orifice is in fluid communication with the bore of an appropriately-sized needle.

Figure 28:
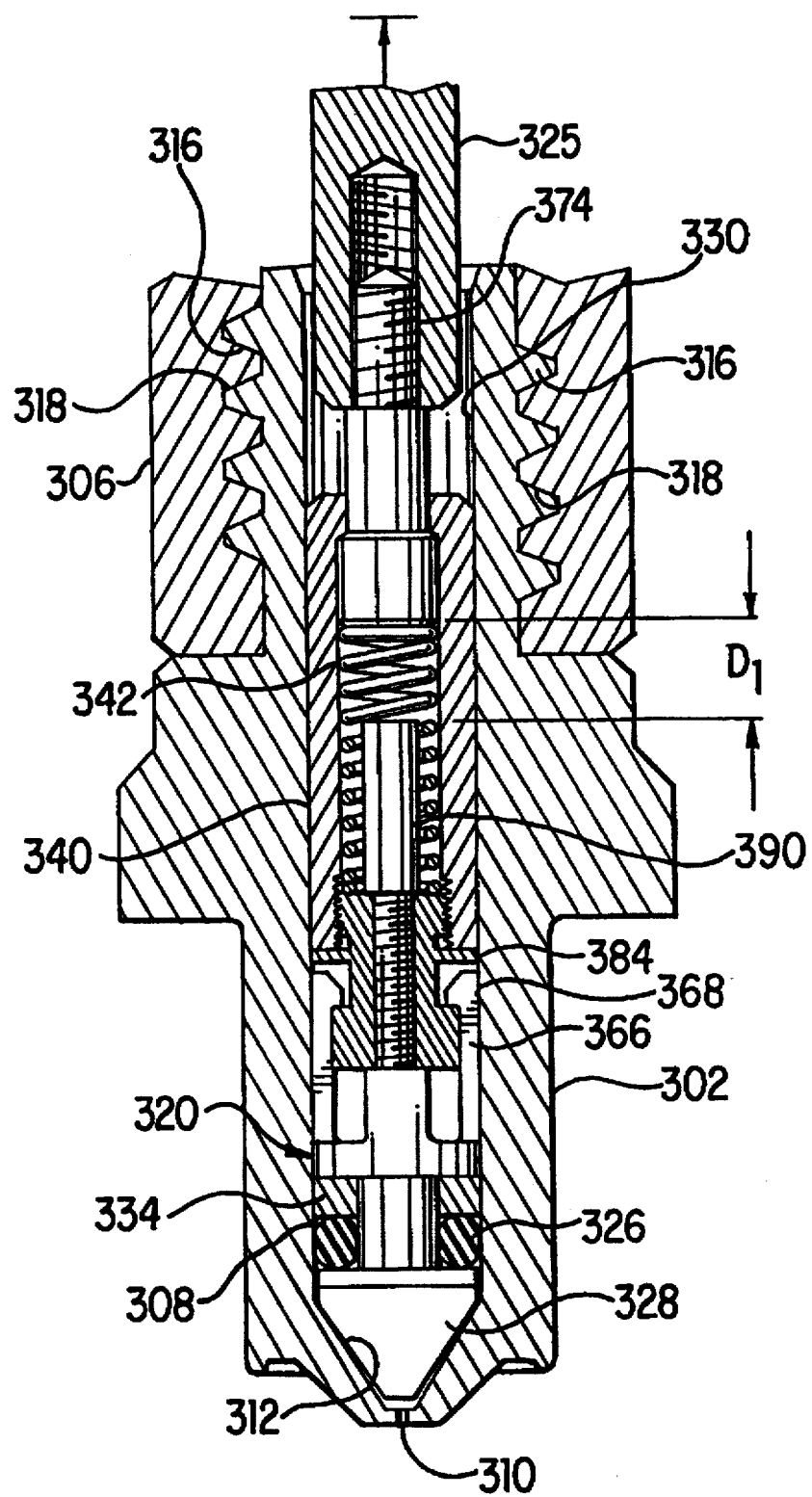
FIG. 28 is a view similar to FIG. 25 but further including a nozzle body and injector housing shown during a fill phase of operation.
Figures 29, 30:
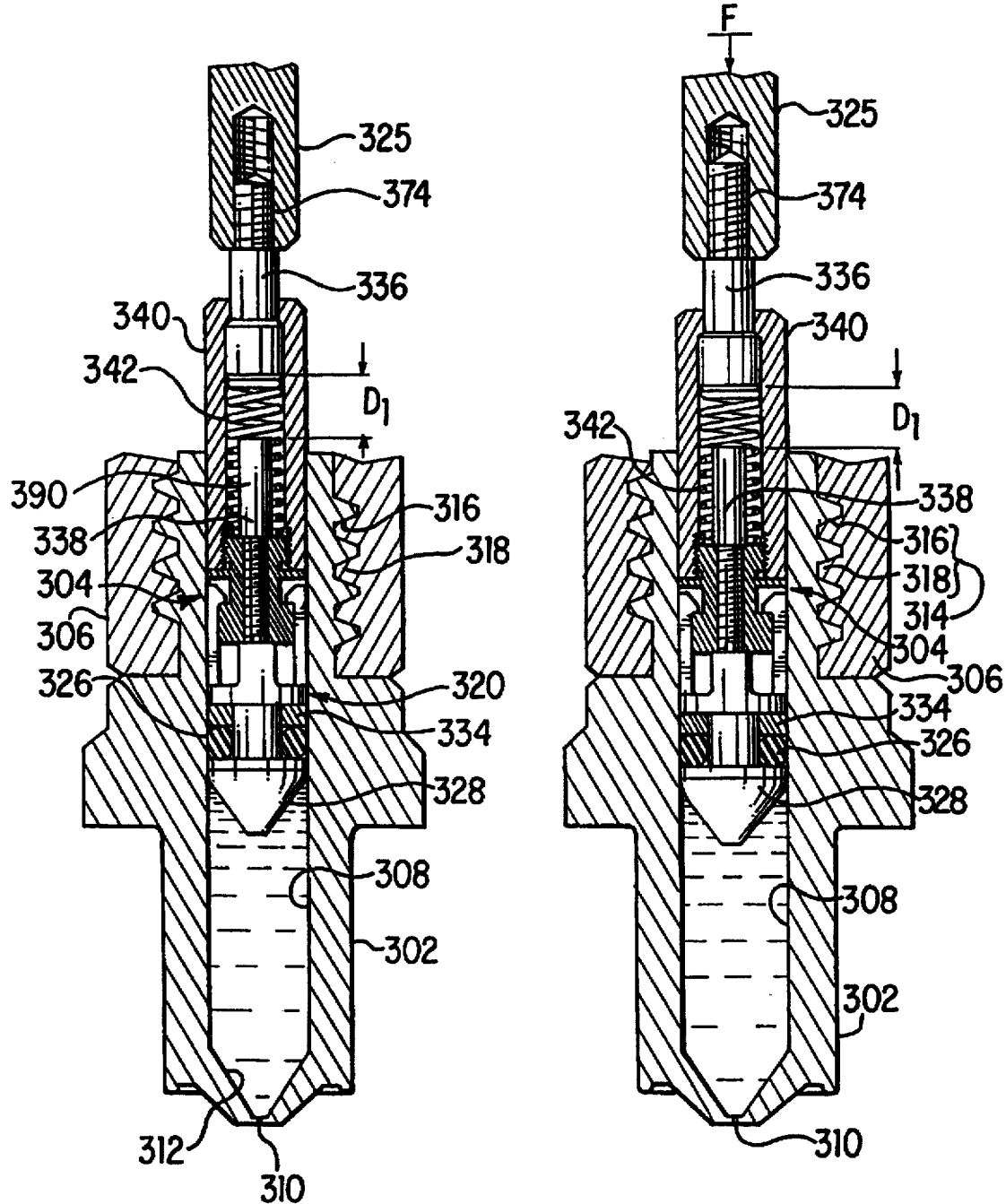
FIG. 29 is a view similar to FIG. 28 but shown during a bleed phase of operation.
FIG. 30 is a view similar to FIG. 28 but shown during a firing initiated phase of operation.
Figure 31:
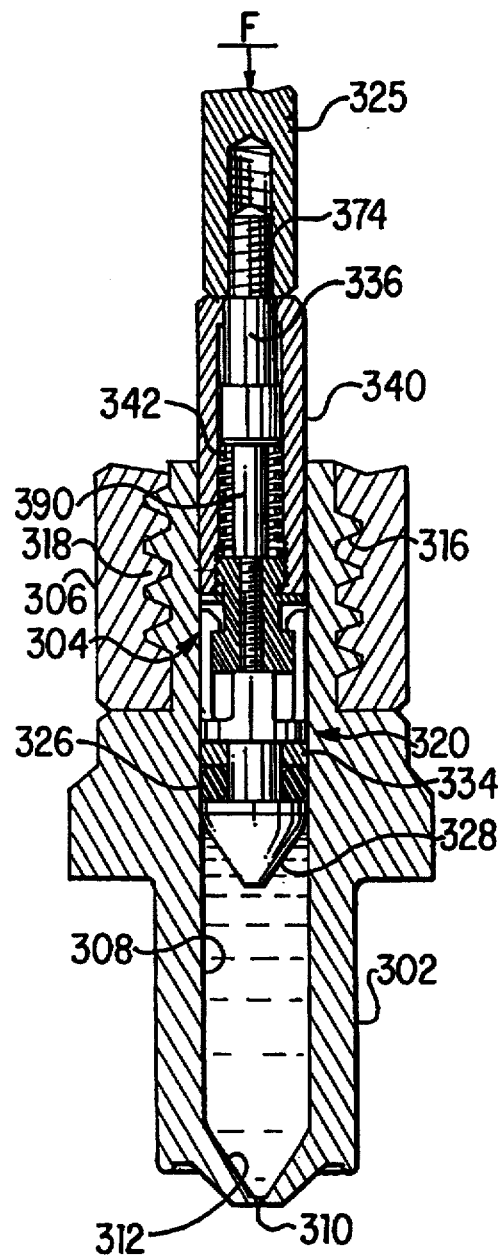
FIG. 31 is a view similar to FIG. 28 but shown during an impact gap closed phase of operation.

Operation of the second embodiment of the plunger/ram assembly 304 will now be described with respect to FIGS. 28–32. The plunger/ram assembly 304 is pushed proximally into the chamber 308, to purge air. FIG. 28 shows the plunger/ram assembly 304 fully pushed, before the desired injection fluid is drawn into the chamber 308. As the plunger/ram assembly 304 is pulled distally, a partial vacuum is established inside the chamber 308 and the desired fluid is drawn into the chamber 308 via the orifice 310, as depicted in FIG. 29.

In the event that air bubbles and/or excess fluid are drawn into the chamber, the plunger/ram assembly 304 must be pushed proximally to expel the bubbles or excess fluid. As shown in FIG. 30, and according to a preferred embodiment of the present invention, spring member 342 has sufficient stiffness to resist relative movement between the pin 336 and the tip 338. Since the spring member 342 is pre-loaded (being compressed within the 340), there is no relative movement between the pin 336 and the tip 338 during the bleeding or purging phase so that the gap $D_1$ or free travel distance between the first and second driving members 338,336 is maintained. It is within the ordinary skill of the art worker to select a proper resilient spring member to accomplish this purpose. Once installed, the preload on the spring member provides a force greater than the force required to move the plunger/ram assembly 304 within the chamber 308 and towards the orifice 310.

Figure 32:
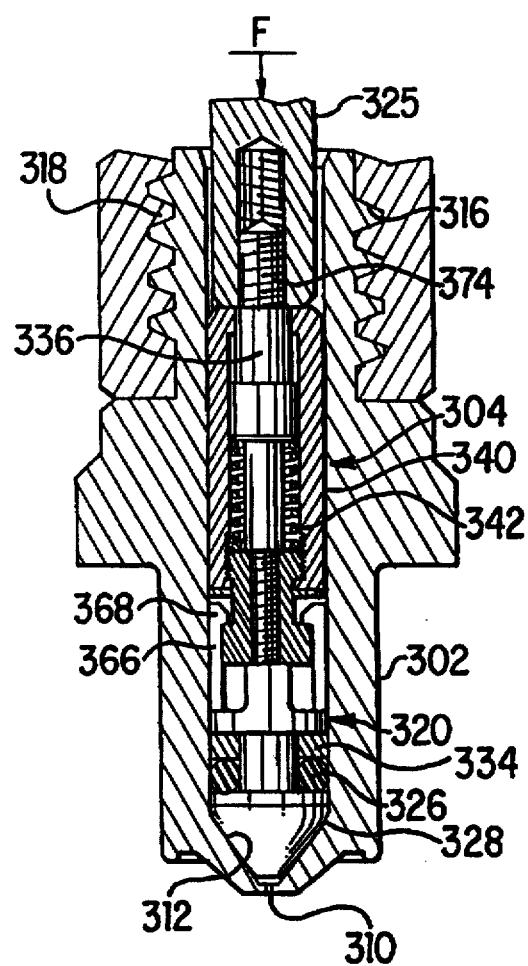
FIG. 32 is a view similar to FIG. 28 but shown during a fired phase of operation.

To inject high pressure fluid, upon application of a relatively large force F on the ram 325, the ram 325 transmits this force F to the second driving member or pin 336. This force F compresses the resilient spring member 342 and allows the second driving member 336 to travel across the gap $D_1$ and directly transmit the force to the first driving member or tip 338. The tip 338 thereby proximally moves the plunger 324 towards the orifice 310 to eject fluid out of the chamber 308, as shown in FIG. 32. If the plunger/ram assembly 304 is to be reused by the same patient, the pin 336 is pulled distally by the ram 325 as depicted in FIG. 29 and, due to the resiliency of the spring member 342, the first and second distances $D_{11}$, $D_2$ are accurately reestablished or restored.

After fluid injection is completed, the nozzle body 302 can be rotated until the threads are free of the corresponding threads on the injector housing so that the nozzle body 302 can be removed from the injector housing. The plunger 324 can be disposed of and the tip 338 can be replaced with another tip having a tail portion 390 of different length to change the free travel between the first and second driving members.

In a normal operation of the fluid injector, the ram 325 of the injection device is operatively connected to an energy source and imparts a sudden force or impact F to the pin 336, which force is high enough to compress the spring member 342 and to allow the pin 336 to directly drive the tip 338 and plunger 324 towards the orifice 310. This action is sufficient to drive the fluid contained in the chamber 308 outward through the orifice 310 at a relatively high peak jet stream pressure of, for example, in excess of 5,000 psi. By "high pressure", what is meant is a jet stream pressure which is capable of penetrating the skin of a patient. This would be a pressure of greater than 1,000 psi and typically between about 3,000 and 10,000 psi.

The first distance or gap $D_l$ plays an important role in creating the preferred pressure spike necessary to pierce through the patient's skin or other portion of the patient's body. Changing the magnitude of the gap $D_1$ will change the initial force imparted on the tip and plunger. The peak pressure thus can be varied by varying the gap $D_1$. It can also vary depending upon the viscosity of the fluid to be injected, the desired injection penetration depth and other parameters which may affect the initial injection pressure output. One of ordinary skill in the art can determine by routine experimentation the optimum gap for any plunger assembly that is to be used with a particular injection fluid. Advantageously, tip, pin, and/or the whole ram assembly can be manufactured with different indicia such as different color codes and/or other markings, wherein each different indicia denotes a resulting predetermined length of gap $D_1$. This indicia coding scheme will easily assist the user in choosing a proper nozzle assembly for a specific application.

Also, in an alternative embodiment, the first distance $D_1$ between the distal end of the tip 336 and the proximal end of the pin 338 is chosen to be greater than the second distance $D_2$. In this arrangement, the sleeve 340 functions to be directly impacted by the ram 325 which moves the tip 338 and plunger 324 towards the orifice 310.

The nozzle body 302 can be connected to the injector housing using any known structure for attaching and detaching two components together. The present invention preferably contemplates a bayonet mount, which has diametrically opposed threads. These threads are first aligned in an opening having a similar cross-sectional configuration provided in the injector housing so that the threads can be inserted. Thereafter, the nozzle body is rotated relative to the injector housing by a predetermined degree to prevent the nozzle body from detaching in the axial direction. The bayonet-mount enables a quick attachment and detachment of the nozzle body as well as the disposable plunger. Other connection means can be used, if desired for a particular application.

It should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A nozzle assembly adapted for use with an injector device having an energy generating source, comprising:
    a chamber adapted for holding a fluid and having first and second end portions with an orifice defined at the first end portion for passage of the fluid and being open at the second end portion;
    a first driving member movably positioned in said chamber;
    a second driving member movably positioned in said chamber and spaced apart from the first driving member according to a predetermined travel distance and including an end portion operative for expelling fluid out of or drawing fluid into the chamber via the orifice; and
    a spacing member disposed between the first and second driving members for maintaining said predetermined travel distance during displacement of the first and second driving members before the energy generating source is activated.

2. The nozzle assembly of claim 1 wherein the spacing member comprises a frangible connection between the first and second driving members, wherein when said energy generating source is activated, a force is produced which breaks the frangible connection and drives the second driving member across said predetermined travel distance toward the first driving member for urging the first driving member towards the chamber orifice to expel fluid therefrom.

3. The nozzle assembly of claim 1, wherein the first driving member includes a seal member to prevent fluid from exiting the chamber around the first driving member and through the open end and the frangible connection has a smaller cross-sectional area than either of the first and second driving members.

4. The nozzle assembly of claim 1 wherein the second driving member includes an end post which can be grasped to move the second driving member in a direction away from the chamber orifice to either draw fluid into the chamber or to remove the second driving member from the chamber, and wherein, after firing, the first driving member remains in the chamber to prevent reuse of the nozzle assembly.

5. The nozzle assembly of claim 1 wherein the first and second driving members are manufactured with indicia representative of a predetermined travel distance, so that different travel distances can be provided by selection of first and second driving members having different indicia.

6. The nozzle assembly of claim 5, wherein said indicia includes a specific color code, selected from different color codes, corresponding to a respective predetermined travel distance between the first and second driving members.

7. The nozzle assembly of claim 1 wherein the chamber includes a tapered portion adjacent the orifice and the first driving member includes a tapered cone which conforms to the tapered portion of the chamber; the first and second driving members are cylindrical and have D-shaped end portions which face each other; and the frangible connection comprises a rectangular bridge connecting straight sides of the D-shaped portions of the first and second driving members.

8. The nozzle assembly of claim 1 wherein the spacing member comprises a resilient biasing member disposed between the first and second driving members for resiliently maintaining said predetermined travel distance.

9. The nozzle assembly of claim 8 wherein said resilient biasing member is a spring; the first and second driving members are operatively connected by a sleeve member; and the spring is disposed within the sleeve member between the driving members.

10. The nozzle assembly of claim 9, wherein the first driving member has a seal in contact with an inner wall of the chamber to prevent fluid from exiting the chamber around the first driving member and through the open end; the chamber includes a tapered portion adjacent the orifice and the first driving member includes a tapered cone which conforms to the tapered portion of the chamber; and the distal end of the first driving member is positioned within the sleeve for contacting a proximal end of the second driving member.

11. The nozzle assembly of claim 8 wherein the resilient biasing member has a preselected preload and is operatively disposed for maintaining said predetermined travel distance when said preload is greater than a movement force applied to the second driving member.

12. The nozzle assembly of claim 11 wherein said first driving member includes a plunger which is removably connected at the forward end thereof for expelling fluid from the chamber orifice.

13. The nozzle assembly of claim 12 wherein said plunger includes a first end portion facing the first driving member and a second end portion adapted to face the orifice of the chamber, said first driving member including a first end portion facing the second driving member and a second end portion facing the first end portion of the plunger, wherein the first end portion of the plunger and the second end portion of the first driving member include releasable engagement means which form the removable connection.

14. The nozzle assembly of claim 13 wherein the releasable engagement means is adapted to cooperate with the chamber so as to be maintained in an engaged state when the nozzle assembly is positioned within the chamber, and can be disengaged when removed from the chamber.

15. The nozzle assembly of claim 11 wherein said first driving member includes a tail portion facing the second driving member, said tail portion having a preselected length which controls said predetermined travel distance.

16. The nozzle assembly of claim 15 wherein said tail portion of the first driving member has an adjustable length to selectively vary the predetermined travel distance.

17. A nozzle assembly adapted for a needleless hypodermic fluid injector having a ram and a nozzle member defining a blind bore and at least one orifice communicating with said bore, said nozzle assembly comprising;

a first driving member;

a second driving member selectively spaced apart from the first driving member according to a free travel distance;

a plunger member adapted to be movably positioned within said bore, said bore and movable plunger member collectively defining a variable-volume fluid chamber communicating with said orifice, said plunger member adapted to be selectively movable by the ram between a first position at which the fluid chamber has a minimum volume, a second position at which the fluid chamber has a maximum volume, and an intermediate position at which the fluid chamber has an intermediate volume smaller than the maximum volume and greater than the minimum volume, said plunger member and first and second driving members operatively connected to each other for selectively expelling fluid from and drawing fluid into the chamber, and the second driving member being spaced apart from the first driving member by a preselected free travel distance; and a member operative for maintaining said free travel distance when the plunger assembly is moved from its second position to its intermediate position and for collapsing said free travel distance when the plunger assembly is moved from its intermediate position to its first position.

18. The nozzle assembly of claim 17, wherein said plunger member is removably connected to the first driving member.

19. The nozzle assembly of claim 18, wherein said plunger member is disposable.

20. An injection device comprising a housing, an energy source, a trigger mechanism for activating the energy source and a nozzle assembly according to claim 1.

21. The device of claim 20 wherein the nozzle assembly is removably attached to the housing and is disposable.

* * * * *

UNITED STATES PATENT AND TRADEMARK OFFICE
CERTIFICATE OF CORRECTION

PATENT NO. : 5,697,917            Page 1 of 2

DATED : December 16, 1997

INVENTORS : Sadowski et al.

It is certified that error appears in the above-identified patent and that said Letters Patent is hereby corrected as shown below:

Column 8, line 55: after "270," insert --as shown in Figs. 7, 9 and 10,--.

Column 10, line 1: delete "distally".

Column 11, line 32: after "injector housing" insert --306--.

Column 11, line 44: after "plunger assembly" insert --304, as shown in Figs. 16 and 17,--.

Column 11, line 52: after "seal member" insert --326--.

Column 11, line 53: delete "is".

Column 12, line 26: change "second" to --first--; and change "first" to --second--.

Column 12, line 49: change "(*e.g.*, pin 336)" to --(*e.g.*, pin) 336--.

Column 13, line 16: change "(*e.g.*, pin 336)" to --(*e.g.*, pin) 336--.

Column 13, line 26: change "(*e.g.*, tip 338)" to --(*e.g.*, tip) 338--.

Column 13, line 42: after "portion" insert --390--.

UNITED STATES PATENT AND TRADEMARK OFFICE
CERTIFICATE OF CORRECTION

PATENT NO. : 5,697,917
DATED : December 16, 1997
INVENTOR(S) : Sadowski, et al

It is certified that error appears in the above-identified patent and that said Letters Patent is hereby corrected as shown below:

Column 14, line 6: after "within the" insert --sleeve--.

Signed and Sealed this

Twenty-eighth Day of April, 1998

Attest:

BRUCE LEHMAN

Attesting Officer

Commissioner of Patents and Trademarks